United States Patent
Myung et al.

(10) Patent No.: US 8,853,294 B2
(45) Date of Patent: Oct. 7, 2014

(54) POLYURETHANE-GRAFTED HYDROGELS

(71) Applicants: David Myung, Santa Clara, CA (US); Lampros Kourtis, Berkeley, CA (US); Robert Ward, Berkeley, CA (US); Michael J. Jaasma, San Francisco, CA (US); Keith McCrea, Concord, CA (US)

(72) Inventors: David Myung, Santa Clara, CA (US); Lampros Kourtis, Berkeley, CA (US); Robert Ward, Berkeley, CA (US); Michael J. Jaasma, San Francisco, CA (US); Keith McCrea, Concord, CA (US)

(73) Assignees: Biomimedica, Inc., Berkeley, CA (US); Emergence Venture Partners, LLC, Berkeley, CA (US)

( * ) Notice: Subject to any disclaimer, the term of this patent is extended or adjusted under 35 U.S.C. 154(b) by 0 days.

(21) Appl. No.: 13/905,028

(22) Filed: May 29, 2013

(65) Prior Publication Data
US 2013/0261212 A1    Oct. 3, 2013

Related U.S. Application Data

(63) Continuation of application No. 12/536,233, filed on Aug. 5, 2009, now Pat. No. 8,497,023.

(60) Provisional application No. 61/086,442, filed on Aug. 5, 2008.

(51) Int. Cl.
*A61L 27/26*    (2006.01)

(52) U.S. Cl.
USPC ............................................ 522/86; 523/115

(58) Field of Classification Search
USPC .......... 522/86; 524/115; 514/16.7, 17.1, 17.2; 623/23.58
See application file for complete search history.

(56) References Cited

U.S. PATENT DOCUMENTS

| | | |
|---|---|---|
| 3,030,327 A | 4/1962 | Hosch |
| 3,053,251 A | 9/1962 | Black et al. |
| 3,702,611 A | 11/1972 | Fishbein |
| 3,826,678 A | 7/1974 | Hoffman et al. |
| 3,833,404 A | 9/1974 | Sperling et al. |
| 3,939,049 A | 2/1976 | Ratner et al. |
| 4,035,848 A | 7/1977 | Wagner |
| 4,128,600 A | 12/1978 | Skinner et al. |
| 4,192,827 A | 3/1980 | Mueller et al. |
| 4,224,699 A | 9/1980 | Weber |
| 4,302,553 A | 11/1981 | Frisch et al. |
| 4,312,079 A | 1/1982 | Dorre et al. |
| 4,320,709 A | 3/1982 | Hladun |
| 4,391,797 A | 7/1983 | Folkman et al. |
| 4,423,099 A | 12/1983 | Mueller et al. |
| 4,439,583 A | 3/1984 | Gould et al. |
| 4,452,925 A | 6/1984 | Kuzma et al. |
| 4,468,499 A | 8/1984 | Siegfried et al. |

(Continued)

FOREIGN PATENT DOCUMENTS

| | | |
|---|---|---|
| EP | 1779875 A1 | 5/2007 |
| GB | 2372707 A | 9/2002 |

(Continued)

OTHER PUBLICATIONS

Bobyn et al., The optimum pore size for the fixation of porous-surfaced metal implants by the ingrowth of bone. Clin Orthop Relat Res, Jul./Aug. 1980(150): p. 263-70.

(Continued)

*Primary Examiner* — Thao T. Tran
(74) *Attorney, Agent, or Firm* — Shay Glenn LLP

(57) ABSTRACT

An article comprising two chemically grafted polymer layers comprising a hydrogel layer and an end-functionalized polyurethane layer. The invention also includes methods of making and using the article.

20 Claims, 11 Drawing Sheets

(56) References Cited

U.S. PATENT DOCUMENTS

| | | | |
|---|---|---|---|
| 4,477,604 | A | 10/1984 | Oechsle, III |
| 4,487,865 | A | 12/1984 | Balazs et al. |
| 4,500,676 | A | 2/1985 | Balazs et al. |
| 4,502,161 | A | 3/1985 | Wall |
| 4,536,554 | A | 8/1985 | Lim et al. |
| 4,575,539 | A | 3/1986 | DeCrosta et al. |
| 4,621,637 | A | 11/1986 | Fishbein |
| 4,678,468 | A | 7/1987 | Hiroyoshi |
| 4,680,336 | A | 7/1987 | Larsen et al. |
| 4,693,715 | A | 9/1987 | Abel, Jr. |
| 4,836,884 | A | 6/1989 | McAuslan |
| 4,846,841 | A | 7/1989 | Oh |
| 4,865,601 | A | 9/1989 | Caldwell et al. |
| 4,913,144 | A | 4/1990 | Del Medico |
| 4,931,287 | A | 6/1990 | Bae et al. |
| 4,966,934 | A | 10/1990 | Huang et al. |
| 4,973,493 | A | 11/1990 | Guire |
| 4,978,352 | A | 12/1990 | Fedorov et al. |
| 5,030,230 | A | 7/1991 | White |
| 5,067,961 | A | 11/1991 | Kelman et al. |
| 5,087,392 | A | 2/1992 | Burke et al. |
| 5,094,876 | A | 3/1992 | Goldberg et al. |
| 5,100,689 | A | 3/1992 | Goldberg et al. |
| 5,112,350 | A | 5/1992 | Civerchia et al. |
| 5,115,056 | A | 5/1992 | Mueller et al. |
| 5,122,133 | A | 6/1992 | Evans |
| 5,133,769 | A | 7/1992 | Wagner et al. |
| 5,171,318 | A | 12/1992 | Gibson et al. |
| 5,258,024 | A | 11/1993 | Chavel et al. |
| 5,264,495 | A | 11/1993 | Irie et al. |
| 5,276,070 | A | 1/1994 | Arroyo |
| 5,282,851 | A | 2/1994 | Jacob-LaBarre |
| 5,290,548 | A | 3/1994 | Goldberg |
| 5,300,116 | A | 4/1994 | Chirila et al. |
| 5,314,478 | A | 5/1994 | Oka et al. |
| 5,374,515 | A | 12/1994 | Parenteau et al. |
| 5,403,893 | A | 4/1995 | Tanaka et al. |
| 5,476,515 | A | 12/1995 | Kelman |
| 5,556,429 | A | 9/1996 | Felt |
| 5,562,738 | A | 10/1996 | Boyd et al. |
| 5,589,563 | A | 12/1996 | Ward |
| 5,591,170 | A | 1/1997 | Spievack et al. |
| 5,643,390 | A | 7/1997 | Don et al. |
| 5,644,049 | A | 7/1997 | Giusti et al. |
| 5,645,592 | A | 7/1997 | Nicolais et al. |
| 5,656,210 | A | 8/1997 | Hill et al. |
| 5,660,692 | A | 8/1997 | Nesburn et al. |
| 5,674,942 | A | 10/1997 | Hill et al. |
| 5,693,034 | A | 12/1997 | Buscemi et al. |
| 5,716,633 | A | 2/1998 | Civerchia |
| 5,733,289 | A | 3/1998 | Seedhom et al. |
| 5,763,529 | A | 6/1998 | Lucas |
| 5,770,669 | A | 6/1998 | Robertson et al. |
| 5,800,412 | A | 9/1998 | Zhang et al. |
| 5,824,079 | A | 10/1998 | Siegler et al. |
| 5,836,313 | A | 11/1998 | Perez et al. |
| 5,856,366 | A | 1/1999 | Shiveley et al. |
| 5,904,927 | A | 5/1999 | Amiji |
| 5,913,858 | A | 6/1999 | Calandruccio et al. |
| 5,962,005 | A | 10/1999 | Saga et al. |
| 5,976,648 | A | 11/1999 | Li et al. |
| 6,001,894 | A | 12/1999 | Ottersbach et al. |
| 6,005,160 | A | 12/1999 | Hsiue et al. |
| 6,027,742 | A | 2/2000 | Lee et al. |
| 6,031,017 | A | 2/2000 | Waki et al. |
| 6,057,406 | A | 5/2000 | Pojman et al. |
| 6,120,904 | A | 9/2000 | Hostettler et al. |
| 6,160,084 | A | 12/2000 | Langer et al. |
| 6,171,300 | B1 | 1/2001 | Adams |
| 6,210,438 | B1 | 4/2001 | Sheets, Jr. et al. |
| 6,214,044 | B1 | 4/2001 | Silverstrini |
| 6,221,467 | B1 | 4/2001 | Nazarova et al. |
| 6,224,893 | B1 | 5/2001 | Langer et al. |
| 6,231,605 | B1 | 5/2001 | Ku |
| 6,231,611 | B1 | 5/2001 | Mosseri |
| 6,239,209 | B1 | 5/2001 | Yang et al. |
| 6,251,965 | B1 | 6/2001 | Wang et al. |
| 6,254,637 | B1 | 7/2001 | Lee et al. |
| 6,264,695 | B1 | 7/2001 | Stoy |
| 6,265,016 | B1 | 7/2001 | Hostettler et al. |
| 6,281,271 | B1 | 8/2001 | Rumphost et al. |
| 6,306,177 | B1 | 10/2001 | Felt et al. |
| 6,331,578 | B1 | 12/2001 | Turner et al. |
| 6,368,315 | B1 | 4/2002 | Gillis et al. |
| 6,372,815 | B1 | 4/2002 | Sulc et al. |
| 6,376,742 | B1 | 4/2002 | Zdrahala et al. |
| 6,388,043 | B1 | 5/2002 | Langer et al. |
| 6,391,055 | B1 | 5/2002 | Ikada et al. |
| 6,428,576 | B1 | 8/2002 | Haldimann |
| 6,437,018 | B1 | 8/2002 | Gertzman et al. |
| 6,440,444 | B2 | 8/2002 | Boyce et al. |
| 6,479,565 | B1 | 11/2002 | Stanley |
| 6,482,209 | B1 | 11/2002 | Engh et al. |
| 6,494,917 | B1 | 12/2002 | McKellop et al. |
| 6,509,098 | B1 | 1/2003 | Merrill et al. |
| 6,610,067 | B2 | 8/2003 | Tallarida et al. |
| 6,629,997 | B2 | 10/2003 | Mansmann |
| 6,632,235 | B2 | 10/2003 | Weikel et al. |
| 6,632,246 | B1 | 10/2003 | Simon et al. |
| 6,645,715 | B1 | 11/2003 | Griffith et al. |
| 6,652,587 | B2 | 11/2003 | Felt et al. |
| 6,673,079 | B1 | 1/2004 | Kane |
| 6,673,112 | B2 | 1/2004 | Nigam |
| 6,679,917 | B2 | 1/2004 | Ek |
| 6,689,165 | B2 | 2/2004 | Jacob et al. |
| 6,726,322 | B2 | 4/2004 | Andino et al. |
| 6,733,533 | B1 | 5/2004 | Lozier |
| 6,740,087 | B2 | 5/2004 | Knox |
| 6,755,865 | B2 | 6/2004 | Tarabishy |
| 6,846,875 | B2 | 1/2005 | Pennings et al. |
| 6,852,125 | B2 | 2/2005 | Simon et al. |
| 6,866,936 | B2 | 3/2005 | Opolski |
| 6,911,212 | B2 | 6/2005 | Gertzman et al. |
| 6,918,914 | B2 | 7/2005 | Bauer |
| 6,921,264 | B2 | 7/2005 | Mayer et al. |
| 6,949,251 | B2 | 9/2005 | Dalal et al. |
| RE38,839 | E | 10/2005 | Magnante |
| 6,953,594 | B2 | 10/2005 | Lee et al. |
| 6,955,540 | B2 | 10/2005 | Mayer et al. |
| 6,960,617 | B2 | 11/2005 | Omidian et al. |
| 6,976,997 | B2 | 12/2005 | Noolandi et al. |
| 7,008,226 | B2 | 3/2006 | Mayer et al. |
| 7,008,635 | B1 | 3/2006 | Coury et al. |
| 7,018,460 | B2 | 3/2006 | Xu et al. |
| 7,019,192 | B2 | 3/2006 | Gertzman et al. |
| 7,029,479 | B2 | 4/2006 | Tallarida et al. |
| 7,037,984 | B2 | 5/2006 | Lendlein et al. |
| 7,049,351 | B2 | 5/2006 | Phelan et al. |
| 7,066,958 | B2 | 6/2006 | Ferree |
| 7,083,650 | B2 | 8/2006 | Moskowitz et al. |
| 7,094,286 | B2 | 8/2006 | Liu |
| 7,105,026 | B2 | 9/2006 | Johnson et al. |
| 7,160,305 | B2 | 1/2007 | Schmieding |
| 7,163,541 | B2 | 1/2007 | Ek |
| 7,176,247 | B1 | 2/2007 | Walker, Jr. |
| 7,204,897 | B2 | 4/2007 | Stoy et al. |
| 7,217,294 | B2 | 5/2007 | Kusanagi et al. |
| 7,235,592 | B2 | 6/2007 | Muratoglu et al. |
| 7,279,174 | B2 | 10/2007 | Pacetti et al. |
| 7,279,507 | B2 | 10/2007 | Hu et al. |
| 7,303,814 | B2 | 12/2007 | Lamberti et al. |
| 7,335,205 | B2 | 2/2008 | Aeschlimann et al. |
| 7,341,593 | B2 | 3/2008 | Auxepaules et al. |
| 7,371,257 | B2 | 5/2008 | Sahatjian et al. |
| 7,387,810 | B2 | 6/2008 | Hossainy |
| 7,468,075 | B2 | 12/2008 | Lang et al. |
| 7,476,398 | B1 | 1/2009 | Doillon et al. |
| 7,563,483 | B2 | 7/2009 | Hossainy et al. |
| 7,618,462 | B2 | 11/2009 | Ek |
| 7,678,151 | B2 | 3/2010 | Ek |
| 7,713,305 | B2 | 5/2010 | Ek |
| 7,824,666 | B2 | 11/2010 | Wolff et al. |
| 8,497,023 | B2 | 7/2013 | Myung et al. |
| 2002/0055007 | A1 | 5/2002 | Soane et al. |

(56) References Cited

U.S. PATENT DOCUMENTS

| | | |
|---|---|---|
| 2002/0082699 A1 | 6/2002 | Ward et al. |
| 2002/0091229 A1 | 7/2002 | Hubbell et al. |
| 2002/0173855 A1 | 11/2002 | Mansmann |
| 2002/0198280 A1 | 12/2002 | Baba et al. |
| 2003/0022216 A1 | 1/2003 | Mao et al. |
| 2003/0083389 A1 | 5/2003 | Kao et al. |
| 2003/0092777 A1 | 5/2003 | Leitner |
| 2003/0100666 A1 | 5/2003 | DeGroot et al. |
| 2003/0114936 A1 | 6/2003 | Sherwood et al. |
| 2003/0130741 A1 | 7/2003 | McMinn |
| 2003/0153981 A1 | 8/2003 | Wang et al. |
| 2003/0170308 A1 | 9/2003 | Cleary et al. |
| 2004/0028804 A1 | 2/2004 | Anderson et al. |
| 2004/0034437 A1 | 2/2004 | Schmieding |
| 2004/0044410 A1 | 3/2004 | Ferree et al. |
| 2004/0059425 A1 | 3/2004 | Schmieding |
| 2004/0116564 A1 | 6/2004 | Devlin et al. |
| 2004/0133275 A1 | 7/2004 | Mansmann |
| 2004/0134502 A1 | 7/2004 | Mizuno et al. |
| 2004/0138382 A1 | 7/2004 | Dous |
| 2004/0139382 A1 | 7/2004 | Kim |
| 2004/0147466 A1 | 7/2004 | Barman et al. |
| 2004/0147927 A1 | 7/2004 | Tsougarakis et al. |
| 2004/0153040 A1 | 8/2004 | Martineau et al. |
| 2004/0153079 A1 | 8/2004 | Tsougarakis et al. |
| 2004/0153163 A1 | 8/2004 | Posner |
| 2004/0167528 A1 | 8/2004 | Schantz |
| 2004/0171740 A1 | 9/2004 | Ruberti et al. |
| 2004/0199250 A1 | 10/2004 | Fell |
| 2004/0204760 A1 | 10/2004 | Fitz et al. |
| 2004/0214914 A1 | 10/2004 | Marmo |
| 2004/0230315 A1 | 11/2004 | Ek |
| 2004/0236424 A1 | 11/2004 | Berez et al. |
| 2004/0266941 A1 | 12/2004 | Houston et al. |
| 2004/0267363 A1 | 12/2004 | Fell et al. |
| 2005/0004306 A1 | 1/2005 | Lubnin et al. |
| 2005/0013793 A1 | 1/2005 | Beckman et al. |
| 2005/0027364 A1 | 2/2005 | Kim et al. |
| 2005/0038520 A1 | 2/2005 | Binette et al. |
| 2005/0049459 A1 | 3/2005 | Hern |
| 2005/0055044 A1 | 3/2005 | Kangas |
| 2005/0065616 A1 | 3/2005 | Ankorina-Stark et al. |
| 2005/0090612 A1 | 4/2005 | Soane et al. |
| 2005/0113836 A1 | 5/2005 | Lozier et al. |
| 2005/0113928 A1 | 5/2005 | Cragg et al. |
| 2005/0126680 A1 | 6/2005 | Aeschlimann et al. |
| 2005/0142162 A1 | 6/2005 | Hunter et al. |
| 2005/0147685 A1 | 7/2005 | Osada et al. |
| 2005/0171604 A1 | 8/2005 | Michalow |
| 2005/0187146 A1 | 8/2005 | Helmus et al. |
| 2005/0215660 A1 | 9/2005 | Tomikawa et al. |
| 2005/0218541 A1 | 10/2005 | Peng et al. |
| 2005/0228161 A1 | 10/2005 | Benz et al. |
| 2005/0251267 A1 | 11/2005 | Winterbottom et al. |
| 2005/0251268 A1 | 11/2005 | Truncale |
| 2005/0267482 A1 | 12/2005 | Hyde, Jr. |
| 2005/0267584 A1 | 12/2005 | Burdulis, Jr. et al. |
| 2005/0278025 A1 | 12/2005 | Ku et al. |
| 2005/0283255 A1 | 12/2005 | Geremakis et al. |
| 2005/0287187 A1 | 12/2005 | Mansmann |
| 2006/0008506 A1 | 1/2006 | De Sousa et al. |
| 2006/0052878 A1 | 3/2006 | Schmieding |
| 2006/0083773 A1 | 4/2006 | Myung et al. |
| 2006/0105295 A1 | 5/2006 | Mayer et al. |
| 2006/0111726 A1 | 5/2006 | Felt et al. |
| 2006/0122543 A1 | 6/2006 | Mayer et al. |
| 2006/0134186 A1 | 6/2006 | Carlton et al. |
| 2006/0142406 A1 | 6/2006 | Schmitt et al. |
| 2006/0188487 A1 | 8/2006 | Thomas et al. |
| 2006/0188940 A1 | 8/2006 | Cima et al. |
| 2006/0224244 A1 | 10/2006 | Thomas et al. |
| 2006/0233855 A1 | 10/2006 | Seliktar et al. |
| 2006/0235517 A1 | 10/2006 | Hodorek |
| 2006/0235539 A1 | 10/2006 | Blunn et al. |
| 2006/0235542 A1 | 10/2006 | Hodorek et al. |
| 2006/0241759 A1 | 10/2006 | Trieu |
| 2006/0246241 A1 | 11/2006 | Kruger et al. |
| 2006/0282169 A1 | 12/2006 | Felt et al. |
| 2006/0287721 A1 | 12/2006 | Myung et al. |
| 2006/0287730 A1 | 12/2006 | Segal et al. |
| 2007/0014828 A1 | 1/2007 | Fitzhugh et al. |
| 2007/0016211 A1 | 1/2007 | Botimer |
| 2007/0048382 A1 | 3/2007 | Meyer et al. |
| 2007/0067032 A1 | 3/2007 | Felt et al. |
| 2007/0068816 A1 | 3/2007 | Solomon et al. |
| 2007/0078388 A1 | 4/2007 | Kangas |
| 2007/0078518 A1 | 4/2007 | Lavi |
| 2007/0083266 A1 | 4/2007 | Lang |
| 2007/0088444 A1 | 4/2007 | Hodorek et al. |
| 2007/0098675 A1 | 5/2007 | Elisseeff et al. |
| 2007/0099840 A1 | 5/2007 | Ulijn et al. |
| 2007/0100457 A1 | 5/2007 | Hyde, Jr. et al. |
| 2007/0118218 A1 | 5/2007 | Hooper |
| 2007/0126982 A1 | 6/2007 | Myung et al. |
| 2007/0134291 A1 | 6/2007 | Ting et al. |
| 2007/0135922 A1 | 6/2007 | Trieu |
| 2007/0141108 A1 | 6/2007 | Thomas et al. |
| 2007/0149441 A1 | 6/2007 | Aeschlimann et al. |
| 2007/0167541 A1 | 7/2007 | Ruberti et al. |
| 2007/0179605 A1 | 8/2007 | Myung et al. |
| 2007/0179607 A1 | 8/2007 | Hodorek et al. |
| 2007/0179622 A1 | 8/2007 | Denoziere et al. |
| 2007/0191963 A1 | 8/2007 | Winterbottom et al. |
| 2007/0198022 A1 | 8/2007 | Lang et al. |
| 2007/0202148 A1 | 8/2007 | Ringeisen et al. |
| 2007/0224238 A1 | 9/2007 | Mansmann et al. |
| 2007/0225823 A1 | 9/2007 | Hawkins et al. |
| 2007/0233240 A1 | 10/2007 | Frank et al. |
| 2007/0233269 A1 | 10/2007 | Steines et al. |
| 2007/0265704 A1 | 11/2007 | Mayer et al. |
| 2007/0270783 A1 | 11/2007 | Zumsteg et al. |
| 2007/0276394 A1 | 11/2007 | Johnson et al. |
| 2008/0058954 A1 | 3/2008 | Trieu |
| 2008/0070086 A1 | 3/2008 | Fukuchi et al. |
| 2008/0077249 A1 | 3/2008 | Gradel |
| 2008/0103505 A1 | 5/2008 | Fransen |
| 2008/0124376 A1 | 5/2008 | Pruitt et al. |
| 2008/0241214 A1 | 10/2008 | Myung et al. |
| 2008/0269370 A1 | 10/2008 | Myung et al. |
| 2008/0317818 A1 | 12/2008 | Griffith et al. |
| 2009/0035344 A1 | 2/2009 | Thomas et al. |
| 2009/0062408 A1 | 3/2009 | Liu et al. |
| 2009/0062423 A1 | 3/2009 | Betz et al. |
| 2009/0088846 A1 | 4/2009 | Myung et al. |
| 2009/0142508 A1 | 6/2009 | Lai |
| 2009/0163860 A1 | 6/2009 | Patrick et al. |
| 2009/0176891 A1 | 7/2009 | Chogle et al. |
| 2009/0209966 A1 | 8/2009 | Chandler |
| 2009/0221730 A1 | 9/2009 | Kowalski et al. |
| 2009/0233887 A1 | 9/2009 | Shalaby et al. |
| 2009/0240337 A1 | 9/2009 | Myung et al. |
| 2009/0312807 A1 | 12/2009 | Boudreault et al. |
| 2010/0010114 A1 | 1/2010 | Myung et al. |
| 2010/0056646 A1 | 3/2010 | Shalaby et al. |
| 2010/0125341 A1 | 5/2010 | Frauens |
| 2011/0152868 A1 | 6/2011 | Kourtis et al. |
| 2012/0045651 A1 | 2/2012 | Myung et al. |
| 2012/0116531 A1 | 5/2012 | Forsell |
| 2012/0209396 A1 | 8/2012 | Myung et al. |
| 2012/0232657 A1 | 9/2012 | Myung et al. |
| 2012/0277807 A1 | 11/2012 | Myung et al. |
| 2013/0096691 A1 | 4/2013 | Myung et al. |
| 2013/0103157 A1 | 4/2013 | Kourtis et al. |
| 2013/0131741 A1 | 5/2013 | Kourtis et al. |
| 2013/0138210 A1 | 5/2013 | Myung et al. |
| 2013/0138211 A1 | 5/2013 | Myung et al. |

FOREIGN PATENT DOCUMENTS

| | | |
|---|---|---|
| JP | 06-287443 A | 10/1994 |
| JP | 09-077809 A | 3/1997 |
| JP | 10-500038 | 1/1998 |
| JP | 3176176 | 4/2001 |
| JP | 2002-514233 A | 5/2002 |

(56) References Cited

FOREIGN PATENT DOCUMENTS

| | | |
|---|---|---|
| JP | 2002-518564 A | 6/2002 |
| JP | 2002-518565 A | 6/2002 |
| JP | 2003-171475 A | 6/2003 |
| JP | 2004-512079 | 4/2004 |
| JP | 2004-515311 | 5/2004 |
| JP | 2005-305162 | 11/2005 |
| JP | 2006-517842 | 8/2006 |
| JP | 2007-501674 | 2/2007 |
| WO | WO 94/01468 A1 | 1/1994 |
| WO | WO 00/02937 A1 | 1/2000 |
| WO | WO 00/043050 A1 | 7/2000 |
| WO | WO02/26848 A2 | 4/2002 |
| WO | WO 2004/055057 A1 | 7/2004 |
| WO | WO 2004/091685 A2 | 10/2004 |
| WO | WO2007/067697 A2 | 6/2007 |
| WO | WO 2007/112305 A2 | 10/2007 |
| WO | WO 2009/071937 A1 | 6/2009 |
| WO | WO2010/037685 | 4/2010 |
| WO | WO 2010/059495 A2 | 5/2010 |

OTHER PUBLICATIONS

Borden et al.; The sintered microsphere matrix for bone tissue engineering: In vitroosteoconductivity studies; J. Biomed. Mat. Res.; 61(3); pp. 421-429; Sep. 2002.

Brodbeck et al., Biomaterial adherent macrophage apoptosis is increased by hydrophilic and anionic substrates in vivo. Proc Natl Acad Sci U S A, Aug. 6, 2002. 99(16): p. 10287-92.

Brown et al.; Solvent/Non-solvent sintering: A novel route to create porous microsphere scaffolds for tissue regeneration; J. Biomed. Mat. Res. (Part B: Applied Biomaterials); 86B(2); pp. 396-406; Aug. 2008.

Causton et al.; Dental materials: 1981 literature review Part 1; Journal of Dentistry; vol. 12; Issue 1; pp. 1R28; Mar. 1984.

Charnley, J.; Anchorage of the femoral head prosthesis to the shaft of the femur; J Bone Joint Surg Br.; 42-B:28-30; Feb. 1960.

Covert et al.; Friction characteristics of a potential articular cartilage biomaterial. Wear, Aug. 2003. 255: p. 1064-1068.

Depuy Orthopaedics; Bone Cement Time Setting Chart, product file; date of publication unknown; available to applicants at least as of Jul. 2012.

Dror et al.; Gradient interpenetrating polymer networks. I. Poly(ether urethane) and polyacrylamide IPN; J of Applied Polymer Science; 26; pp. 1741-1757; Jun. 1981.

Elmer's Products Inc.; Material Safety Data Sheet; "Elmer's Nano Glue"; Jun. 13, 2007.

Elsabee et al.; Gradient interpenetrating polymer networks. II. Polyacrylamide gradients in poly(ether urethane); J of Applied Polymer Science; 28(7); pp. 2151-2166; Jun. 1983.

Evans et al.; The use of corneal organ culture in biocompatibility studies; Biomaterials; vol. 23; pp. 1359-1367; Mar. 2002.

Frank, Curt; Structure-property relationships for hydrogels with applications to biomedical devices; Presentation at American Chemical Society Mtg; San Francisco, CA; Sep. 11, 2006.

Gao et al.; Grafting of hydrophilic monomers onto polyurethane membranes by solution or pre-absorbing methods for acceleration of cell compatibility; Chinese Journal of Polymer Science; vol. 19; No. 5; pp. 493-498; Oct. 20, 2001.

Gong et al.; Double-network hydrogels with extremely high mechanical strength; Adv. Mater.; vol. 15; No. 14; pp. 1155-1158; Jul. 17, 2003.

Gorna et al.; Preparation, degradation, and clarification of biodegradable polyurethane foams for bone graft substitutes; J. Biomed Mater Res A; 67(3); pp. 813-827; Dec. 1, 2003.

Guelcher et al.; Synthesis and in vitro biocompatibility of injectable polyurethane foam scaffolds; Tissue Engineering; 12(5); pp. 1247-1259; May 2006.

Guelcher et al.; Synthesis of biocompatible segmented polyurethanes from aliphatic diisocyanates and diurea diol chain extenders; Acta biomaterialia; 1(4); pp. 471-484; Jul. 2005.

Gunatillake et al.; Designing biostable polyurethane elastomers for biomedical implants; Aust. J. Chem.; vol. 56; pp. 545-557; Jun. 2003.

Hern et al.; Incorporation of adhesion peptides into nonadhesive hydrogels useful for tissue resurfacing; J. Biomed. Materials Research; vol. 39; No. 1; pp. 266-276; Feb. 1998.

Iwasaki et al., Hydrogel like elastic membrane consisting of semi-interpenetrating polymer networks based on a phosphorylcholine polymer and a segmented polyurethane; J. Polym. Sci Part A: Polym Chem; 41; pp. 68-75; Jan. 2003.

Khan et al., Analysis and evaluation of a biomedical polycarbonate urethane tested in an in vitro study and an ovine arthroplasty model. Part I: materials selection and evaluation. Biomaterials, Feb. 2005. 26(6): p. 621-31.

Kim et al.; Water sorption of ploy(propylene glycol)/poly(acrylic acid) interpenetrating polymer network hydrogels; Reactive & Functional Polymers; vol. 55; pp. 69-73; Feb. 2003.

Kim et al.; Electrochemical behavior of an interpenetrating polymer network hydrogel composed of poly (propylene glycol) and poly(acrylic acid); Journal of Applied Polymer Science; vol. 89; pp. 2301-2305; Aug. 2003.

Kim et al.; Electrical/pH Responsive Properties of Poly(2-acrylamido-2-methylpropane sulfonic acid)/Hyaluronic Acid Hydrogels; Journal of Applied Polymer Science; vol. 92; issue 3; pp. 1731-1736; May 2004.

Kwong et al.; A comparison of the shrinkage of commercial bone cements when mixed under vacuum; J Bone Joint Surg Br.; 88(1):120-2; Jan. 2006.

Lamba et al.; Polyurethanes in Biomedical Application; CRC Press; pp. 11, 14, 16, 18-20, 57-59, 73, 79 & 104; Nov. 1997.

Lee et al.; Interpenetrating polymer network hydrogels based on poly (ethylene glycol) macromer and chitosan; Carbohydrate Polymer; vol. 41; No. 2; pp. 197-205; Feb. 2000.

Lewis G.; Properties of acrylic bone cement: state of the art review; J Biomed Mater Res.; 38(2):155-82; Summer Jun.-Aug. 1997.

Lipatov et al.; Gradient interpenetrating polymer networks; Journal of Materials Science; 30(4); pp. 1095-1104; Feb. 1995.

Lu et al.; Release behavior of high molecular weight solutes from poly(ethylene glycol)-based degradable networks; Macromolecules; vol. 33(7); pp. 2509-2515; Mar. 2000.

Maroudas et al.; Permeability of articular cartilage; Nature; vol. 219(5160); pp. 1260-1261; Sep. 21, 1968.

Morgan et al.; Dependence of yield strain of human trabecular bone on anatomic site; J Biomech.; 34(5):569-77; May 2001.

Mow et al., Basic Orthopaedic Biomechanics and Mechano-Biology, Lippincot Williams and Wilkins, 3rd Edition, Apr. 2005, pp. 459-461.

Myung, David; Structure, properties, and medical device applications of mechanically enhanced, biometric hydrogel alloys; Doctoral Thesis; Stanford University; Dec. 2007.

Myung et al.; Biomimetic strain hardening in interpenetrating polymer network hydrogels; Polymer, ; vol. 48; No. 18; pp. 5376-5387; Jun. 2007.

Ohman et al.; Mechanical testing of cancellous bone from the femoral head: experimental errors due to off-axis measurements; J Biomech.; 40(11):2426-33; (year of publication is sufficiently earlier than the effective U.S. filed and any foreign priority date) 2007.

Orr et al.; Shrinkage stresses in bone cement; Biomaterials; 24 (17):2933-40; Aug. 2003.

Park et al.; Synthesis of PVA/PVP hydrogels having two-layer by radiation and their physical properties; Radiation Physics and Chemistry; 67(3-4); pp. 361-365; Jun. 2003.

Puska et al.; Exothermal Characteristics and Release of Residual Monomers from Fiber-reinforced Oligomer-modified Acrylic Bone Cement; J Biomat App; 20:51-64; Jul. 2005.

Saito et al.; Preparation and properties of transparent cellulose hydrogels; J. Applied Polymer Science; 90(11); pp. 3020-3025; Dec. 2003.

Scholes et al.; Compliant layer acetabular cups: friction tsting of a range of materials and designs for a new generation of prosthesis that mimics the natural joint; Proc. IMechE; vol. 220(5); Part H; J. Engineering in Medicine; pp. 583-596, Jul. 2006.

Shalaby; U.S. Appl. No. 61/069,046 entitled "Hydroswellable, segmented, aliphatic polyurethanes and polyurethane ureas," filed Mar. 12, 2008.

(56) References Cited

OTHER PUBLICATIONS

Spector et al.; Porous polymers for biological fixation. Clin Orthop Relat Res, Oct. 1988 (235): p. 207-19.

Stammen et al., Mechanical properties of a novel PVA hydrogel in shear and unconfined compression. Biomaterials, Apr. 2001. 22(8): p. 799-806.

Stryker Orthopaedics; SimplexTM P Bone Cement; Product Literature LSB Rev. 3, Mar. 2006.

Tariq et al.; (Abstract) Sodium benzoate attenuates iminodipropionitrile-induced behavioral syndrome in rats. Behav pharmacol; Dec. 2004.

Tawfik, Dan; Amidation of carboxyl groups; The Protein Protocols Handbook, 2nd Ed.; Humana Press; pp. 477-478; Feb. 2002.

The Engineering Toolbox; Polyurethane insulation: {http://www.engineeringtoolbox.com/polyurethane-insulation-k-values-d_1174.html} pp. 1-3; printed Oct. 21, 2011.

The Engineering Toolbox;Thermal conductivity of some common materials and gases: {http://www.engineeringtoolbox.com/thrmal-conductivity-d_429.html} pp. 1-2; printed Oct. 21, 2011.

The Gorilla Glue Company; Material Safety Data Sheet; "New Fast Cure-Dries White Gorilla Glue®"; Jan. 30, 2007.

The Gorilla Glue Company; Material Safety Data Sheet; "New Stronger-Faster Gorilla Glue®"; Jan. 26, 2007.

Wittemann et al.; Adsorption of proteins on spherical polyelectrolyte brushes in aqueous solution; Phys. Chem. Chem. Phys., Mar. 2003, vol. 5(8), pp. 1671-1677.

Wright et al., Wear studies on prosthetic materials using the pin-on-disc machine. Biomaterials, vol. 3, Issue 1, Jan. 1982, pp. 41R48.

Yang et al.; Preparation of poly(acrylic acid) modified polyurethane membrane for biomaterial by UV radiation without degassing; J. Biomed. Mater. Res.; vol. 45(2); pp. 133-139; May 1999.

Zhu et al.; (Abstract) Promoting the cytocompatibility of polyurethane scaffolds via surface photo-grafting polymerization of acrylamide; J. Mater. Sci. Mater. Med.; vol. 15; No. 3; pp. 283-289; Mar. 2004.

Myung et al.; U.S. Appl. No. 13/816,537 entitled "Hydrophobic and Hydrophilic Interpenetrating Polymer Networks Derived From Hydrophobic Polymers and Methods of Preparing the Same," filed Apr. 24, 2013.

Chen et al.; Mechanical Properties of Polyepichlorohydrin Polyurethane/Poly(methyl methacrylate) IPNs; Chinese J Appl Chem; 12(4):66-69; Aug. 1995 (wEngAbs).

Forsell; U.S. Appl. No. 61/229,735 entitled "Hip Joint Method," filed Jul. 30, 2009.

Hsieh et al.; Compatibility and Morphology in Polyurethane and Polystyrene Ionomeric Interpenetrating Polymer Networks; Polymer Journal; 21(1); pp. 1-10; Jan. 15, 1989.

Ithaca College Gross Anatomy; Joints of the Back; ; 4 pgs. (downloaded Dec. 1, 2013 from http://www.ithaca.edu/faculty/lahr/LE2000/Back/Jointpage.htm).

Jones et al.; Sequential Polyurethane-Poly(Methylmethacrylate) Interpenetrating Polymer Networks as Ureteral Biomaterials: Mechanical Properties and Comparative Resistance to Urinaryencrustation; J Mater Sci Mater Med; 8 (11):713-717; Nov. 1997.

Lam et al.; Update on Ureteral Stents; Urology; 64:9-15; Jul. 2004.

MIT.edu; Material Modulus Properties; 2pgs.; Feb. 8, 2007 (downloaded Nov. 27, 2013 from http://web.archive.org/web/*/http://web.mit.edu/course/3/3.11/www/modules/props.pdf).

Neurosurgical.com; Spinal Anatomy: The Regions of the Spine; 5pgs. (downloaded Dec. 1, 2013 http://www.neurosurgical.com/neuro_medical_info/spinal_anatomy.htm).

Realdictionary; Definition of Implant; 4pgs. (downloaded Dec. 1, 2013 from www.realdictionary.com/?q=implant).

Van Landuyt et al.; Reinforcement of Osteosynthesis Screws with Brushite Cement; Bone; 25(2)(Suppl 1):95S-98S; Aug. 1999.

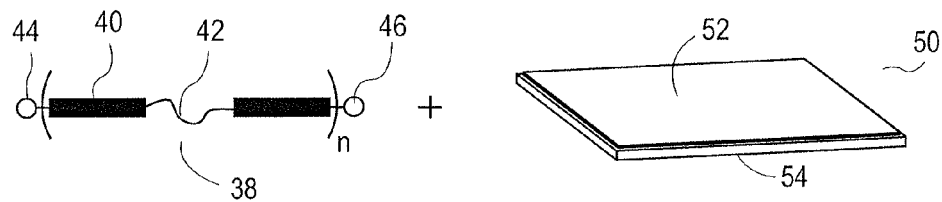
FIG. 5A
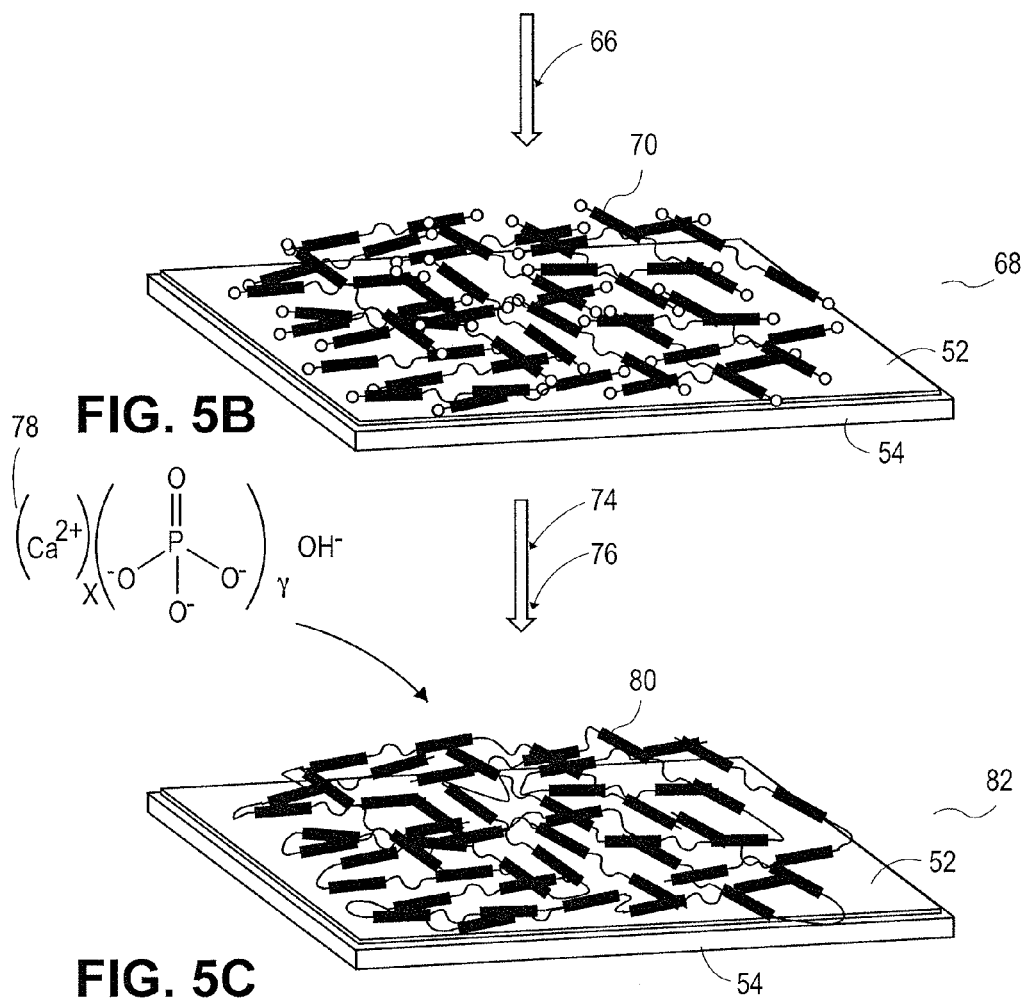
FIG. 5B
FIG. 5C

POLYURETHANE-GRAFTED HYDROGELS

CROSS REFERENCE TO RELATED APPLICATIONS

This application is a continuation of U.S. application Ser. No. 12/536,233, filed Aug. 5, 2009, entitled "Polyurethane-Grafted Hydrogels," which claims priority under 35 U.S.C §119 to U.S. Provisional Patent Application No. 61/086,442, filed Aug. 5, 2008, and entitled "Polyurethane-Grafted Hydrogels," both of which are incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to polymers, and more specifically to methods by which hydrogel and polyurethane polymers are grafted together to form two-layered structures, and by which they are attached to bone, in ways that are useful for medical and commercial devices. The invention also includes materials and articles formed by this method.

BACKGROUND OF THE INVENTION

Some polymer networks take up water and swell. These swollen hydrogels have been created from a variety of starting materials and have been used for a variety of applications. The utility of prior hydrogels for their proposed applications is limited by the properties of these compositions, however. In addition, the starting materials and processes of making and using such prior compositions limit not only the resulting properties of the polymers but also the commercial viability of the manufacturing processes and articles made in such processes. Also, the mechanical properties of the prior polymers are often limited by the mechanical properties of the component polymers used, which in the case of most intrinsically hydrophilic, water-swellable polymers, are usually quite low.

Hydrogels have been combined with polyurethanes to form articles with certain useful properties. Hydrogel materials have been reinforced with polyurethanes and other materials to provide a more robust backing material. Also, a hydrogel coating or overlayer can be added to a hydrophobic polymer article to improve the article's biocompatibility. Prior hydrogel/polyurethane combinations have not provided the best combination of strength and swellability, however. In addition, prior methods of making hydrogel/polyurethane combinations have used expensive and/or toxic processes.

For example, Hoffman et al. U.S. Pat. No. 3,826,678 describes a process for coating an inert polymeric substrate with a reactable hydrogel polymer and then attaching a biologically active molecule in order to make a biocompatible material with a biofunctional surface. Hoffman used "radiation grafting" to attach the hydrogel to the polyurethane and used the reactable hydrogel to attach the biologically active molecules. Hoffman's "radiation grafting" refers to application of expensive high energy to a polymer, a treatment that causes both non-specific formation of bonds and non-specific breaking of bonds. The bonds made are non-specific bonds between the two polymers anywhere along the backbone of the chains, as well as non-specific bonds ("crosslinking") within each polymer. Conditions for using "radiation grafting" were chosen by Hoffman such that more favorable than unfavorable reactions occur.

Hoffman used "radiation grafting" on a preformed material, such as a polyurethane, that had been contacted with a preformed hydrogel or with hydrogel monomers, and then subjected the materials to the high energy radiation (e.g., gamma irradiation or X-rays). The result was crosslinked hydrogel pieces non-specifically grafted to crosslinked polyurethane pieces. Next, the biologically active materials were attached using a specific link that bonded the biomaterial to the hydrogel. In this way, the biological materials were never subject to the fragmentation effects of the radiation treatment, and a bioactive material was made.

Yang et al. (J. Biomed Mater Res 45:133-139, 1999) describe a process for forming a graft material having both polyurethane and hydrogel. Yang formed a mixture of polyurethane, acrylic acid, and photoinitiator, and treated it with UV light in the absence of a degassing step to create an homogeneous and unlayered acrylic acid/polyurethane polymer grafted throughout its composition.

Park and Nho (Radiation Physics and Chemistry; 67 (2003): 361-365) describe making a wound dressing formed from polyurethane and hydrogel layers. First, polyurethane was dissolved in solvent and dried to form a polyurethane layer. Then a mixture of polyvinyl alcohol/poly-N-vinylpyrrolidone, chitosan and glycerin in water was poured onto the already formed polyurethane layer. The material was optionally treated with freeze-thaw cycles. Conditions were chosen to favor cross-linking reactions in the hydrogel over material degradation during irradiation treatment, and the material was subject to gamma irradiation to form a hydrogel. The result was a hydrogel adjacent a polyurethane; Park et al. do not describe the nature of any interaction between the polyurethane layer and the hydrogel layer.

Wang et al. (U.S. Patent Publication 2002/00524480) describe a process for forming a material having a modified surface that can be used to tether other compounds at the surface while maintaining the bulk properties of the material. Wang started with a foamed hydrophobic polymer, such as an acylic or polyurethane, and introduced a functional monomer such as acylate or vinyl monomer, and an initiator just at the polymer surface, such as by limited swelling of the polymer in a solvent. The functional monomer was treated, such as with UV irradiation, to form a second polymer. A surface modification agent, such as heparin, may be attached to the second polymer. The result was an Interpenetrating Polymer Network (IPN) at the surface between the polymerized formed polymer, with only indirect interactions between the first and second polymers, and possibly modified with a modification agent covalently attached to the second polymer.

Gao et al. (Chinese Journal of Polymer Science Vol. 19, No. 5, (2001), 493-498) describe improvements to materials for use in improving long-term implants that become integrated into the body, such as devices put into blood vessels and in artificial hearts. Gao describes two methods to create on a segmented polyurethane a hydrophilic surface containing functional groups that will adhere cells and support growth. In both methods, the segmented polyurethane was activated by a high concentration of toxic hydrogen peroxide (30%) and UV light to generate reactive groups.

In the "Solution Grafting Method," of Gao, the activated segmented polyurethane was immersed in a solution of hydrophilic monomers, such as 2-(dimethylamino)ethyl methacrylate, 2-hydroxyethyl acrylate or acrylamide, and ammonium iron (II) sulfate hexahydrate, and the monomers grafted onto the segmented polyurethane by treatment with UV light. The iron compound prevents any unwanted polymerization of the monomers in solution.

In the "Pre-Absorbing Grafting Method" of Gao, the activated segmented polyurethane membrane was immersed in a solution of hydrophilic monomers, removed, placed under nitrogen, and the hydrophilic monomers grafted onto the reactive groups of the segmented polyurethane by treatment with UV light. The membrane was rinsed with hot water for 48 hours to remove homopolymers. The result was a very thin layer of hydrophilic polymer coating on the surface of the polyurethane. SEM images of materials made using the "Solution Grafting Method" versus those made using "Pre-Absorbing Grafting Method" show significant differences in appearance in materials made using the different methods.

SUMMARY OF THE INVENTION

The present invention improves upon prior articles made from a combination of a hydrogel and a polyurethane and methods of making such articles. The mechanical properties desired for certain medical applications is often outside the range of possibility of many hydrophilic starting materials. Hence, one aspect of this invention takes advantage of the high mechanical strength of hydrophobic starting materials and combines those materials with hydrogels as a useful way to achieve the goal of high mechanical strength in addition to other desirable properties provided by the hydrogels without the cost and issues associated with the use of highly specialized equipment (e.g., $^{60}$Co radiation source) or damage to and/or ambiguity about the composition of the formed material due to lack of specificity in the treatment to effect bonding (e.g., gamma irradiation).

For purposes of this application, an "interpenetrating polymer network" or "IPN" is a material comprising two or more polymer networks which are at least partially interlaced on a molecular scale, but not covalently bonded to each other, and cannot be separated unless chemical bonds are broken.

A "polymer" is a substance comprising macromolecules (comprising repeated units of monomers), including homopolymers and copolymers.

A "copolymer" is a polymer derived from two or more species of monomer.

A "homopolymer" is a polymer derived from a single monomeric species.

A "graft polymer" is a polymer of that has side chains ("graft macromolecules") containing different atoms from those in the main chain. This definition includes side chains that are polymers.

A "graft copolymer" is a graft polymer in which adjacent blocks in the main (or in the side) chains comprise different species of monomer.

One aspect of the invention provides an article having a hydrogel layer chemically grafted to an end-functionalized polyurethane layer. In some embodiments, the hydrogel and polyurethane are interfacially grafted. In some embodiments, the polyurethane layer may be selected from a group consisting of polycarbonate urethane, polycarbonate urethane urea, polyester urethane, polyether urethane, polyurethane urea, or a silicone derivative of these.

The polyurethane may have hard segments, soft segments, chain extenders, and end groups. In some embodiments the hard segments are selected from the group 1,5 naphthalene diisocyanate (NDI), isophorone isocyanate (IPDI), 3,3-bi-toluene diisocyanate (TODI), methylene bis(p-cyclohexyl isocyanate) (H12MDI), cyclohexyl diisocyanate (CHDI), 2,6 tolulene diisocyanate or 2,4 toluene diisocyanate (TDI), hexamethyl diisocyanate (HMDI), and methylene bis(p-phenyl isocyanate) (MDI).

In some embodiments the soft segments of the polyurethane may be selected from the group hydroxy terminated butadiene, hydroxyl terminated polyisobutylene, hydroxybutyl terminated polydimethylsiloxane (PDMS), poly (1,6 hexyl 1,2-ethyl carbonate), hydrogenated polybutadiene, polycaprolactone, polyethylene adipate, polyethylene oxide (PEO), polyhexamethylene carbonate glycol, polypropylene oxide (PPO), polytetramethylene adipate, and poly(tetramethylene oxide) (PTMO).

In some embodiments, the chain extenders of the polyurethane may be selected from the group 1,4 butanediol, ethylene diamine, 4,4' methylene bis(2-chloroaniline) (MOCA), ethylene glycol, and hexane diol.

In some embodiments, the polyurethane endgroups may be selected from the group acylamide, acrylate, allyl ether, methacrylate, or vinyl.

In some embodiments the hydrogel layer may be end-linked macromeric subunits, e.g. PEG or a biomolecule, or polymerized monomeric subunits. In some embodiments, the biomolecule may be, e.g., collagen, one or more growth factors, steroids, bisphosphonates, or combinations or derivatives thereof. In some embodiments the biomolecules may be selected from the group any Bone Morphogenetic Protein, any Fibroblast Growth Factor, any Transforming Growth Factor, or any Osteogenic Protein.

In some embodiments the hydrogel layer may be a homopolymer. In some embodiments the hydrogel may be polymerized monomeric subunits. In some embodiments, the hydrogel layer may be a copolymer. The copolymer may have a polymerized subunit, such as a subunit selected from the group consisting of acrylamide, hydroxyethyl acrylamide, N-isopropyl acrylamide, 2-hydroxyethyl methacrylate, and 2-hydroxyethyl acrylate. In some embodiments, the hydrogel network may contain at least 50%, at least 75%, or at least 90% by dry weight of telechelic macromonomer.

In some embodiments the hydrogel layer may be an IPN with a first and second network. In some embodiments the first IPN network may be end-linked macromeric subunits. In some embodiments, the polymerized macromeric subunits may be selected from the group consisting of PEG, poly(N-vinyl pyrrolidone), polydimethylsiloxane, poly (vinyl alcohol), polysaccharide, and a biomolecule. In some embodiments the polymerized macromeric subunits may have end group or side group functionalities selected from the group consisting of acrylamide, acrylate, allyl, methacrylamide, methacrylate, N-vinyl sulfone, and vinyl.

In some embodiments the second IPN network may be polymerized subunits (monomers). In some embodiments, the subunits may be hydrophilic. The hydrophilic subunit may be ionizable. The ionizable subunit may be anionic. The anionic subunits may include carboxylic acid and/or sulfonic acid groups. In some embodiments, the second network may be polyacrylic acid. In some embodiments, the ionizable subunit may be cationic. In some embodiments, the hydrophilic subunit may be non-ionic. The non-ionic subunit may be selected from the group consisting of acrylamide, methacrylamide, N-hydroxyethyl acrylamide, N-isopropylacrylamide, methyl methacrylate, N-vinyl pyrrolidone, 2-hydroxyethyl methacrylate, 2-hydroxyethyl acrylate, and/or derivatives of these.

In some embodiments both networks of the IPN may be grafted to the polyurethane.

In some embodiments, a second polyurethane may be attached to the first polyurethane. In some embodiments, the second polyurethane may have functionalized end groups. In some embodiments, the second polyurethane may include salt such as salt with crystals of size that varies from 10 μm to 1000 μm. In some embodiments, the second polyurethane may be porous, with the pore size varying, e.g.; from 10 μm to 1000 μm. In some embodiments, the second polyurethane may contain foaming agents to create open cell porosity, with the pore size varying, e.g.; from 10 μm to 1000 μm.

In some embodiments the second polyurethane may include a biomolecule. In some embodiments, the biomolecule may be selected from the group consisting of collagen, bone morphogenetic protein, bisphosphonate, and an osteogenic protein. In some embodiments, the second polyurethane may include a bone component, i.e., a material normally found in natural bone. The bone component may be one or more of carbonated apatite, hydroxyapatite, alpha tricalcium phosphate, beta tricalcium phosphate, and other calcium phosphates.

In some embodiments, the second polyurethane may include entrapped fillers.

In some embodiments, the second polyurethane may include an antioxidant. The antioxidant may be selected from the group consisting of ascorbic acid, beta carotene, glutathione, Irganox®, lipoic acid, retinol, santowhite, uric acid, ubiquinol, and Vitamin E.

Another aspect of the invention provides an article having a first polyurethane, and a second polyurethane attached to the first polyurethane, the second polyurethane having a putty-like hardness. In some embodiments, the second polyurethane has reactive end groups. In some embodiments the second polyurethane may include salt. In some embodiments, the second polyurethane may be porous.

In some embodiments, the composition of the first and second polyurethane may include entrapped fillers.

In some embodiments, the composition of the first and second polyurethane may include an antioxidant. The antioxidant may be selected from the group consisting of ascorbic acid, Vitamin E, Irganox, santowhite, glutathione, uric acid, lipoic acid, beta carotene, retinol, and ubiquinol.

Another aspect of the invention provides a process for grafting a polyurethane to a hydrogel including the following steps: freezing a first solution containing either reactive hydrogel precursors or end-functionalized polyurethane precursors; applying a second solution containing either end-functionalized polyurethane precursors or reactive hydrogel precursors to the first solution; and polymerizing and crosslinking the solutions to form a laminated graft polymer having a polyurethane and a hydrogel.

Another aspect of the invention provides a process for grafting a polyurethane to a hydrogel including the following steps: casting a layer from a solution containing end-functionalized polyurethane precursors; applying a second solution containing reactive hydrogel precursors, the second solution containing a solvent for the polyurethane layer; and polymerizing and crosslinking the solutions to form a laminated graft polymer having a polyurethane and a hydrogel.

In some embodiments the polymerizing step uses UV light or heat.

In some embodiments, the method may include the steps of immersing at least part of the laminated graft polymer in a third solution; the third solution having hydrogel precursors different from the precursors in the first or second solutions; swelling the graft polymer; and polymerizing the third solution to create a graft polymer having a polyurethane and an IPN, whereby the IPN has a second hydrogel network intertwined with a first hydrogel network. In some embodiments the third solution may be a partial solvent for the first hydrogel, and is able to swell the first hydrogel network.

In some embodiments, the solution containing the hydrogel precursors may have telechelic molecules. In various embodiments, the telechelic molecules may be poly(ethylene) glycol with one or more endgroups selected from the group consisting of acrylate, methacrylate, acrylamide, vinyl, or allyl ether.

In some embodiments, the polyurethane solution may have one or more materials selected from the group consisting of vinyl terminated polyurethane, polycarbonate urethane, polyether urethane, polycarbonate urethane urea, polyester urethane, polyurethane urea and silicone derivatives of these.

Another aspect of the invention provides a process for making a material that can be attached to bone, including the following steps: applying a solution that contains a polyurethane precursor having reactive endgroups, and further containing solvent, photoinitiator and crosslinker to a first polyurethane that is grafted to a hydrogel; polymerizing the polyurethane precursor; and treating with heat and convection to remove the solvent to yield a second unreacted telechelic polyurethane surface coated on a polyurethane grafted hydrogel.

In some embodiments, the second polyurethane may be polycarbonate urethane and in others polyether urethane.

In some embodiments, the reactive endgroups may be selected from the group consisting of acrylamide, acrylate, allyl ether, methacrylate, and vinyl. In some embodiments, the solvent may be selected from the group consisting of dimethylacetamide, dimethyl sulfoxide, and tetrahydrofuran.

In some embodiments, the applying step includes applying a salt.

Another aspect of the invention provides a process for attaching an article to a bone, the article including a porous polyurethane having a photointiator and a crosslinker, the method including the steps of placing the porous polyurethane in apposition to the bone; and polymerizing the second polyurethane to attach the article to the bone. In some embodiments, the porous polyurethane contacts and flows into the bone. The article may also include a second polyurethane attached to the porous polyurethane and optionally a hydrogel. In some embodiments, the polymerizing step may include exposing the polyurethane to UV light, heat, or a chemical initiator.

The polyurethane-grafted hydrogels of the present invention have numerous applications in medicine and industry. In orthopaedics, there is a great need for cartilage replacement materials that emulate the properties of natural cartilage. The invention may also be useful in other areas of orthopaedics (in any joint), such as the spine, a disc or facet replacement, or as a bursal replacement. Other applications of the polyurethane-grafted hydrogels are possible, in fields including but not limited to wound care (e.g. as a wound dressing), plastic surgery, urology (e.g. catheters), or cardiology (e.g. as a stent, catheter, or valve material).

The polyurethane-grafted hydrogels are useful as devices in the form of plugs, patches, caps, or cups to repair defects in joint surfaces. A device is comprised of a hydrogel bearing side and a porous polyurethane bone-interface side which are chemically bonded to each other. The hydrogel side provides a lubricious, "cartilage-like" bearing surface while the polyurethane side provides structural reinforcement and facilitates bone adhesion and ingrowth. The bone interface side of the polyurethane-grafted hydrogel is adhered to bone through any of the above mentioned approaches.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5A-C illustrate how a telechelic polyurethane adhesive is deposited on a polyurethane backing layer.

DETAILED DESCRIPTION OF THE INVENTION

Figure 1A:
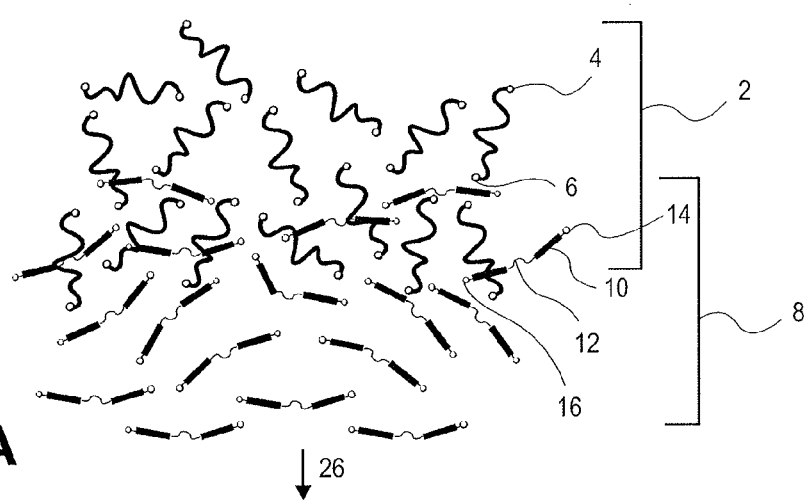
FIGS. 1A-C illustrate a process by which hydrogels and polyurethanes are grafted according to one aspect of this invention.

In one embodiment, a polyurethane is interfacially grafted to a hydrogel to create a layered strong, lubricious polymer graft material. To form the polyurethane grafted hydrogel, monomers or macromonomers of a hydrogel precursor are dissolved with photoinitiator and, optionally, a crosslinker, in an organic solvent or buffer. In some embodiments, monomers or macromonomers of a second hydrogel precursor that will form a copolymer are also dissolved. In some embodiments, biomolecules may be added. Monomers or macromonomers of a polyurethane precursor are also dissolved along with photoinitator, and optionally a crosslinker, in an organic solvent or buffer; the organic solvent or buffer can be the same or different composition as the one in which the hydrogel precursors are dissolved. Additional materials that will give the materials additional properties ("additives") can be added to either or both solutions. The additives can be the same or different in the two solutions.

Any type of organic solvent can be used to create the solutions of the monomers and macromonomers, such as dimethylacetamide, dimethyl sulfoxide, tetrahydrofuran, or chloroform.

Any type of photoinitiator can also be used. This includes, but is not limited to, 2-hydroxy-2-methyl-propiophenone and 2-hydroxy-1-[4-(2-hydroxyethoxy)phenyl]-2-methyl-1-propanone.

Any type of compatible cross-linkers may be used to crosslink the second network in the presence of any of the aforementioned first networks such as, for example, ethylene glycol dimethacrylate, ethylene glycol diacrylate, diethylene glycol dimethacrylate (or diacrylate), triethylene glycol dimethacrylate (or diacrylate), tetraethylene glycol dimethacrylate (or diacrylate), polyethylene glycol dimethacrylate, or polyethylene glycol diacrylate, methylene bisacrylamide, N,N'-(1,2-dihydroxyethylene) bisacrylamide, derivatives, or combinations thereof.

Any monomer or macromonomer may be used to form the polyurethane layer. In some embodiments, the polyurethane has reactive ends. Either one or both ends of the polyurethane may be functionalized. Examples of materials that can be used are polymers having surface active endgroups. See, e.g., Ward et al, U.S. Pat. No. 5,589,563.

In some embodiments, biomolecules (e.g., collagen, growth factors (any Bone Morphogenetic Proteins (BMPs)), Fibroblast Growth Factors (FGFs), Transforming Growth Factors (e.g., TGFβ), Osteogenic Proteins (e.g., OP-1 or osteopontin), steroids (e.g., dexamethasone), and bisphosphonates may be incorporated either as an additive or by covalent linkages, combinations, and/or derivatives thereof. Bone components may also be incorporated into the device, such as hydroxyapatite, carbonated apatite, alpha tricalcium phosphate, beta tricalcium phosphate, combinations, and/or derivatives thereof. The pore size useful for this application ranges between about 10 micrometers to 1000 micrometers.

In one embodiment, the hydrogel precursor solution containing initiator is cast over a mold and flash-frozen in, for example, a liquid nitrogen bath. The polyurethane precursor solution containing initiator is then cast over the surface of the solidified hydrogel precursor solution. The polyurethane precursor solution can be, for example, at room temperature or below. Freezing the first set of precursors before adding the second set prevents major mixing of the two sets of precursors. Polymerization and cross linking is then initiated by UV or heat.

In another embodiment, the polyurethane precursor solution containing initiator is cast over a mold and flash-frozen in, for example, a liquid nitrogen bath. The hydrogel precursor solution containing initiator is then cast over the surface of the solidified polyurethane precursor solution. The hydrogel precursor solution can be, for example, at room temperature or below. Polymerization and cross linking is then initiated by UV or heat.

In another embodiment, the polyurethane precursor solution, (e.g., in dimethylacetamide or tetrahydrofuran), is cast over a mold and dried (e.g., at room temperature), to form a layer. The hydrogel precursor solution, containing at least in part a solvent for the polyurethane layer (e.g., dimethylacetamide or tetrahydrofuran), is applied on the surface of the polyurethane layer. Polymerization and cross linking is initiated by UV or heat.

Figure 1B:
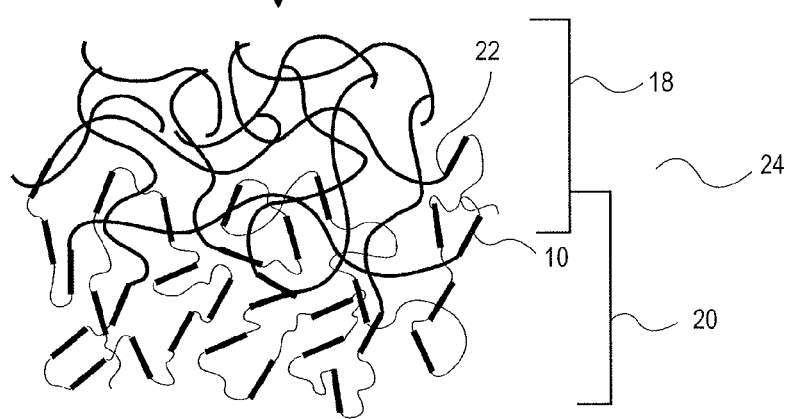
Figure 1C:
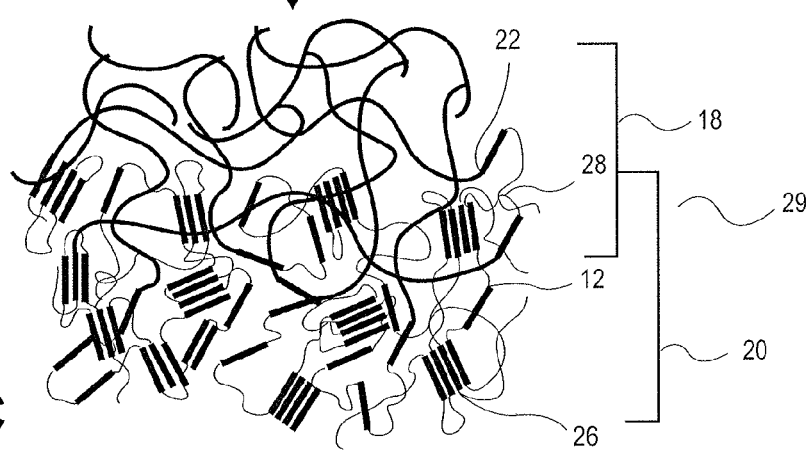

FIGS. 1A-C shows a graft polymer having a polyurethane polymer grafted to a hydrogel polymer, and the method of making, according to the current invention.

FIG. 1A shows two layers of polymer precursors before polymerization. One precursor layer is frozen (e.g., using a liquid nitrogen bath) or otherwise solidified (e.g., by drying) and then a second precursor layer is added to the solidified layer. The figure shows one layer of telechelic hydrogel precursors 2 with functional endgroups 4 and 6. The telechelic ends can be the same or different structures. The figure shows a second layer of telechelic polyurethane precursors 8 with hard segments 10 and soft segments 12. The functional groups, 14 and 16, on the ends of the polyurethane precursor can be the same or different structures. The "bottom" (solidified) layer comprises either set of precursors, and the "top" layer comprises the other set. In one embodiment the telechelic polyurethane precursors 8 may be frozen. In an alternate embodiment, the hydrogel precursors 2 may be frozen. The layered solutions are covered with a glass plate and polymerized through free radical polymerization, using, for example, exposure to UV light 26. Exposure to UV light is thought to have two effects: (1) it initiates polymerization and crosslinking of the two precursor solutions, and (2) it melts at least some of the frozen hydrogel or telechelic polyurethane precursor layer, providing chain mobility at the interface between the two layers, and allowing grafting of the hydrogel to the polyurethane at the interface between the two layers. The process of polymerization may generate additional heat that melts the bulk of the frozen layer, allowing the layer to polymerize and crosslink.

Polymerization leads to the formation of a polyurethane grafted hydrogel material 24, as shown in FIG. 1B. The hydrogel polymer 18 is covalently bound by a graft 22 to the polyurethane polymer 20. The hard segments of the polyurethane polymer 20 assemble to form hard phases 26, as shown in the graft polymer 29 in FIG. 1C. The soft segments assemble in soft phases 28. The use of an end-functionalized polyurethane precursor enables the hydrogel layer to graft to the polyurethane layer using relatively inexpensive UV polymerization while minimizing the amount of initiator (such as hydrogen peroxide) used to facilitate grafting.

Any monomer or macromonomer or biomacromolecule may be used to form the hydrogel polymer network. For convenience, the hydrogel polymer network will be referred to as the "first" network and the polyurethane polymer network as the "second" network; but it should be understood that either solution can be solidified (e.g., frozen or dried) first.

In one embodiment, preformed polyethylene glycol (PEG) macromonomers can be used as the basis of the hydrogel polymer network. PEG is biocompatible, soluble in aqueous solution, and can be synthesized to give a wide range of molecular weights and chemical structures. The hydroxyl end-groups of the bifunctional glycol can be modified into crosslinkable/polymerizeable end-groups to form telechelic PEG molecules with vinyl endgroups such as acrylate, methacrylate, acrylamide, methyacrylamide, vinyl, or allyl ether.

Figure 2A:
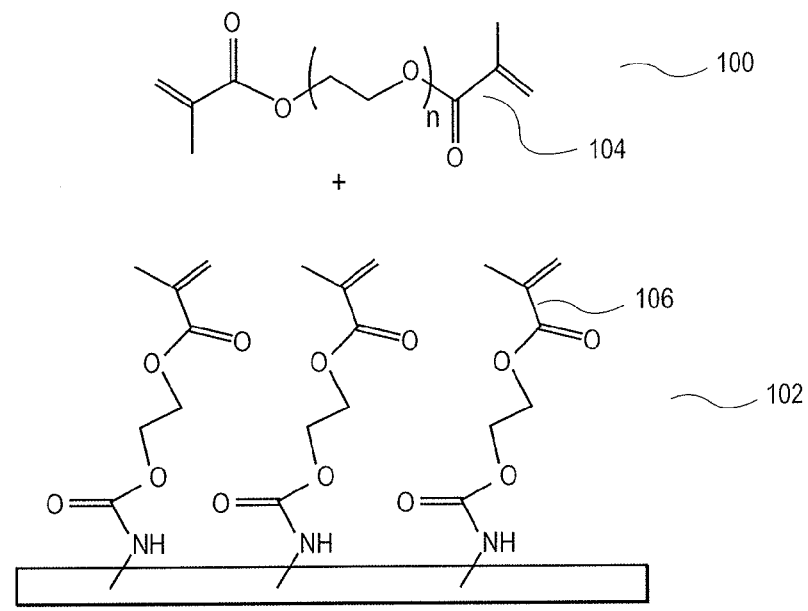
FIGS. 2A-B illustrate one example of a polyethylene glycol (PEG)-dimethacrylate hydrogel grafted to a methacrylate functionalized polyurethane to yield a polyurethane grafted PEG hydrogel.
Figure 2B:
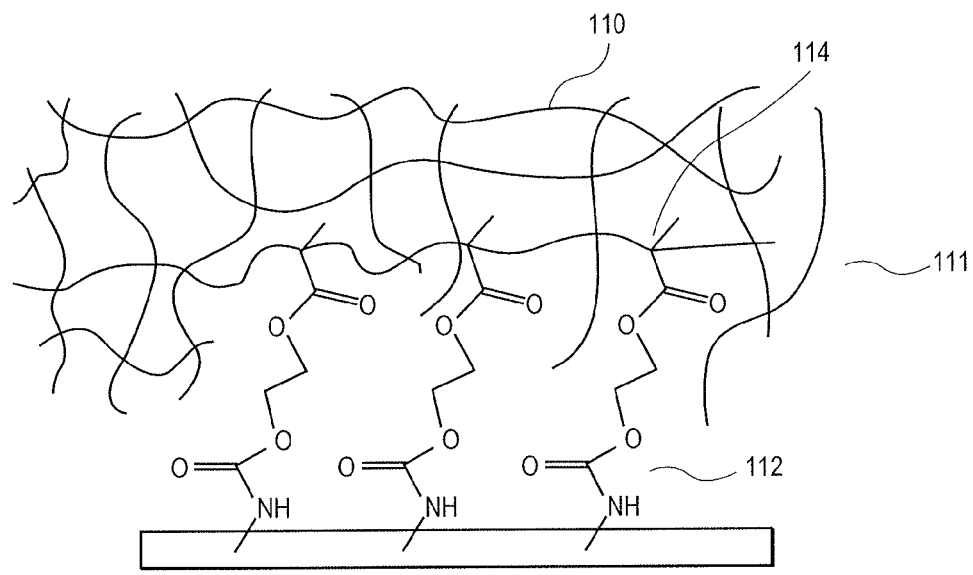

FIGS. 2A-B show a particular example of a graft polymer having a polyurethane polymer grafted to a hydrogel polymer. FIG. 2A shows a poly(ethylene glycol) 100 having reactive dimethylacrylate endgroups 104 being polymerized and crosslinked in the presence of a polyurethane 102 having reactive methacrylate endgroups 106. The result is a polyurethane-grafted PEG hydrogel 111 having a network hydrogel polymer 110 attached via a covalent linkage 114 to a functionalized polyurethane 112. The solvent used can be water or an organic solvent, (e.g., dimethylacetamide or tetrahydrofuran).

In addition to the poly(ethylene glycol), other macromonomers such as polycarbonate, poly(N-vinyl pyrrolidone), polydimethylsiloxane, poly(vinyl alcohol), polysacchrarides (e.g., dextran), biomacromolecules (e.g., collagen) and derivatives or combinations thereof can also be chemically modified with endgroup or side-group functionalities such as acrylates, methacrylates, allyl ethers, vinyls, acrylamides, and methacrylamides and used to form the hydrogel polymer network.

The first network can also be copolymerize with any number of other polymers including but not limited to those based on acrylamide, hydroxyethyl acrylamide, N-isopropylacrylamide, 2-hydroxyethyl methacrylate, 2-hydroxyethyl acrylate or derivatives thereof The polymerized subunit may be a derivative of an acrylate, methacrylate, vinyl, allyl ether, or acrylamide monomer.

Preferably, the dry weight of the first polymer network is at least 50%, more preferably at least 75% by weight, and most preferably at least 95% telechelic macromonomer.

The polyurethane polymer of the second network can be a commercially available material or it can be a new material, including but not limited to a polycarbonate urethane, polycarbonate urethane urea, polyether urethane, segmented polyurethane urea, silicone polycarbonate urethane, or silicone polyether urethane. The molecular weight of the second polymer layer is high enough to provide structural stability to the material. The polyurethane precursor can be vinyl-terminated (on one or both ends) polyurethane, polycarbonate urethane, polycarbonate urethane ureas, polyester urethane, polyether urethane, polyurethane urea, as well as silicone derivatives of these or combinations thereof.

Any type of chemistries and stoichiometries can be used to create the polyurethane polymer. Isocyanates that are used to generate the hard segment include 1,5 naphthalene diisocyanate (NDI), isophorone isocyanate (IPDI), 3,3-bitoluene diisocyanate (TODI), methylene bis(p-cyclohexyl isocyanate) (H12MDI), cyclohexyl diisocyanate (CHDI), 2,6 tolylene diisocyanate or 2,4 toluene diisocyanate (TDI), hexamethyl diisocyanate, or methylene bis(p-phenyl isocyanate).

Chemicals that may be used to generated the soft segment include hydroxy terminated butadiene, hydroxyl terminate polyisobutylene, hydroxybutyl terminated polydimethylsiloxane (PDMS), poly (1,6 hexyl 1,2-ethyl carbonate, and hydrogenated polybutadiene, polycaprolactone, polyethylene adipate, polyethylene oxide (PEO), polyhexamethylene carbonate glycol, polypropylene oxide (PPO), polytetramethylene adipate, and poly(tetramethylene oxide) (PTMO).

Chemicals used as chain extenders include 1,4 butanediol, ethylene diamine, 4,4'methylene bis(2-chloroaniline) (MOCA), ethylene glycol, and hexane diol.

The groups that are used to functionalize the polyurethane macromonomers can be chosen from the same group listed above to functionalize the hydrogel macromoners (e.g., acrylamides, acrylates, allyl ethers, methacrylamides, methacrylates, and vinyls). The functional groups can be on one or both ends, and they can be the same groups or different groups.

Free radical polymerization of the above process may be initiated by other means, such as thermal-initiation and other chemistries not involving the use of ultraviolet light.

Any number of additives can be incorporated into the materials on either the hydrogel side or the polyurethane side. These additives can be included as entrapped fillers or as covalently attached molecules or particles. For instance, antioxidants can be covalently linked into the hydrogel by methacryloxy-functionalization of the anti-oxidant. In one example, a methacrylate group can be regioselectively attached to the primary hydroxyl group of L-ascorbic acid (Vitamin C) by reaction of 2,2,2 trifluoromethyl methacrylate with an immobilized lipase enzyme from Candida Antarctica at 60 degrees Celsius in dioxane in the presence of a polymerization inhibitor (e.g. hydroquinone or di-tert-butyl methyl phenol). Other anti-oxidants can be added, including but not limited to beta carotene, glutathione, Irganox®, lipoic acid, retinol, santowhite, ubiquinol, uric acid, or Vitamin E).

In another embodiment, a second hydrogel network can be added to the first hydrogel network by swelling the hydrogel grafted polyurethane or the first hydrogel network portion of the hydrogel grafted polyurethane in a second solution containing hydrogel precursors with initiator. The second solution may act as a partial solvent for the hydrogel network to swell it without dissolving. The precursors of the second hydrogel network are polymerized inside the first hydrogel network. The result is an interpenetrating polymer network (IPN) grafted to a polyurethane.

Figure 3A:
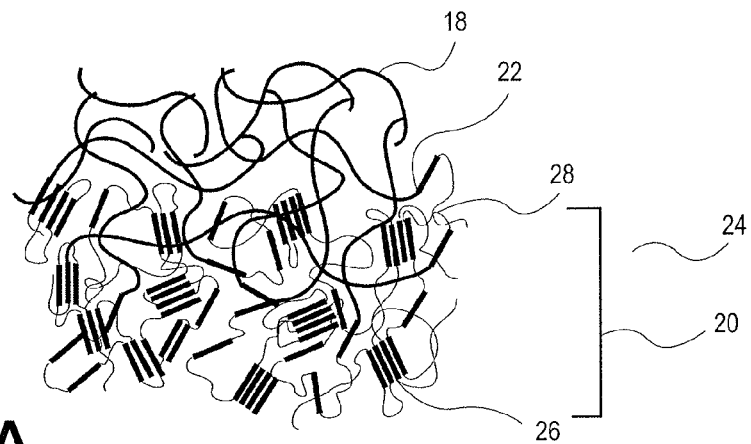
FIGS. 3A-C illustrate how an IPN is formed and grafted to a polyurethane.
Figure 3B:
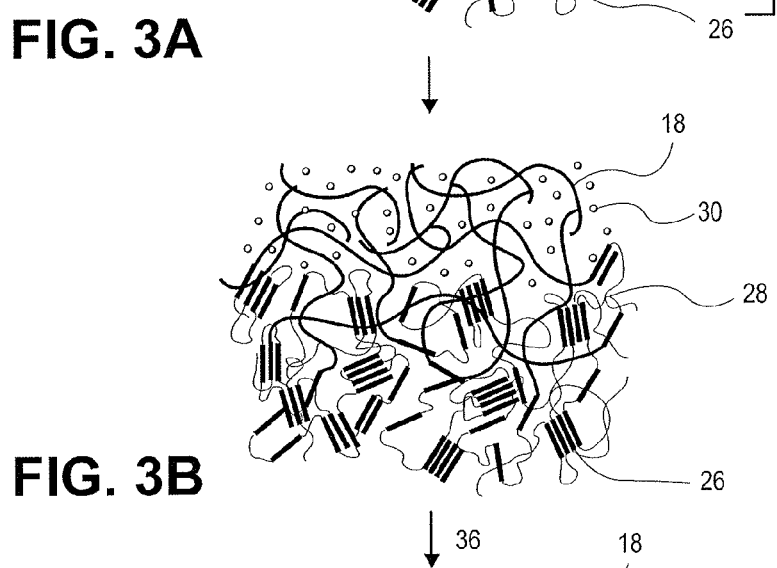
Figure 3C:
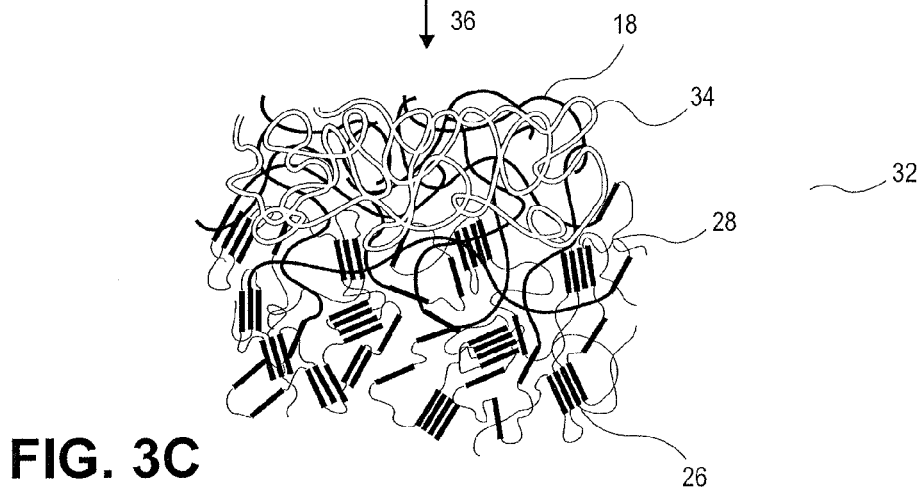

FIGS. 3A-C show an embodiment of a graft polymer having a polyurethane grafted interpenetrating polymer network hydrogel.

FIG. 3A shows a polyurethane grafted hydrogel 24 having a polyurethane polymer 20 grafted to a single hydrogel network 18 via graft linkage 22. The polyurethane polymer 20 has hard phases 26 and soft phases 28. The polymer graft is swollen in a solution of a second hydrogel precursor 30 as shown in FIG. 3B, along with optional crosslinker and photoinitiator (not shown). The second hydrogel precursor 30 is polymerized, as by UV light 36, to form a second hydrogel network 34 interpenetrated within a first hydrogel network 18 as shown in FIG. 3C. The final result is a polyurethane-grafted interpenetrating polymer network hydrogel 32.

In another embodiment, a second hydrogel network can be added to the first hydrogel network. The hydrogel grafted polyurethane is swollen in a second solution containing hydrogel precursors with optional crosslinker and photoinitiator. The second solution may act as a partial solvent for the hydrogel network. Then the precursors of the second hydrogel network are polymerized and crosslinked inside the first hydrogel network to yield a polymer graft, with both hydrogels of the interpenetrating polymer network grafted to polyurethane. The polyurethane second network that is grafted to the first hydrogel network has available reactive groups, such as excess isocyanate.

Figure 4A:
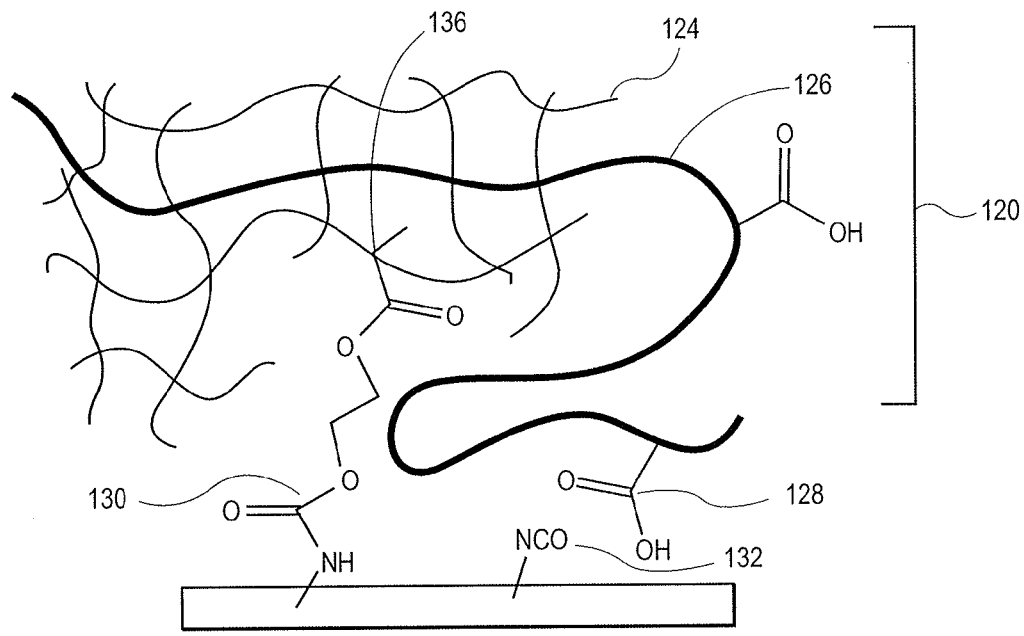
FIGS. 4A-B illustrate how a double polymer graft is formed between polyurethane and a hydrogel IPN.
Figure 4B:
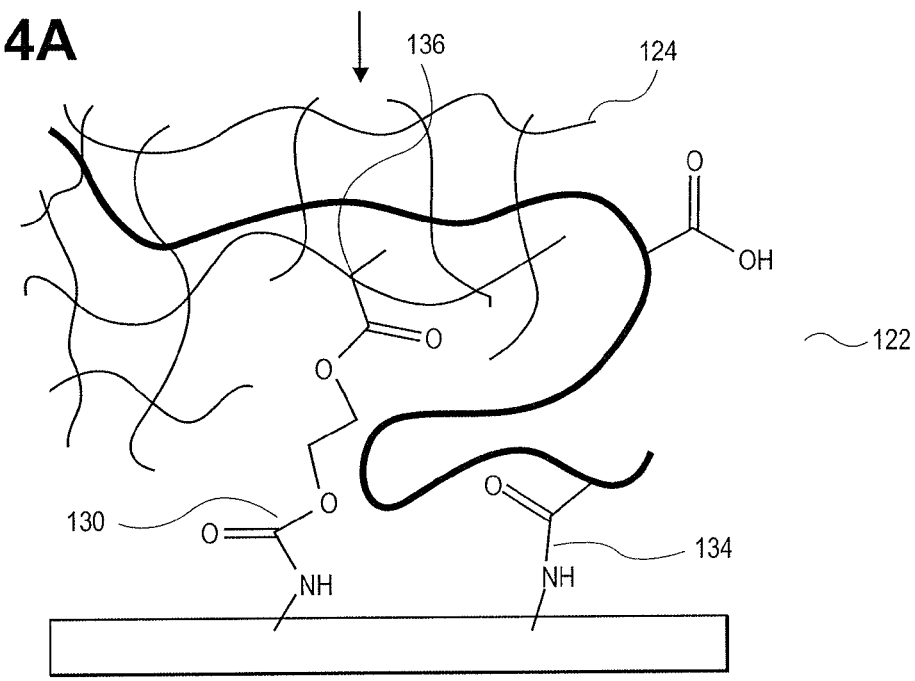

FIGS. 4 A-B show an example of a double graft polymer having a polyurethane polymer grafted to two networks of a hydrogel IPN. FIG. 4A shows a first hydrogel network 124 crosslinked 136 to a polyurethane 130 which has excess functional groups 132 such as isocyanate. The first hydrogel network 124 is entangled with a second hydrogel network 126 forming a hydrogel IPN 120. The second hydrogel network 126 has functional groups 128 such as carboxylate. The functional group 128 of the second hydrogel network interacts with the reactive group 132 of the polyurethane to form a bond 134, and yield a double polymer graft 122, as shown in FIG. 4.

In one embodiment, the hydrophilic precursor in the second hydrogel network is ionizable and anionic (capable of being negatively charged) to yield an ionizable second hydrogel network.

The ionizable second hydrogel polymer network can be poly(acrylic acid) (PAA) hydrogel formed from an aqueous solution of acrylic acid monomers. Other ionizable monomers include ones that contain negatively charged carboxylic acid or sulfonic acid groups, such as 2-acrylamido-2-methylpropanesulfonic acid, methacrylic acid, hyaluronic acid, heparin sulfate, chondroitin sulfate, and derivatives, or combinations thereof.

The second hydrogel network monomer may also be positively charged or cationic.

The hydrophilic precursor for the second hydrogel polymer network may also be non-ionic, such as acrylamide, methacrylamide, N-hydroxyethyl acrylamide, N-isopropylacrylamide, methylmethacrylate, N-vinyl pyrrolidone, 2-hydroxyethyl methacrylate, 2-hydroxyethyl acrylate or derivatives thereof. In other embodiments, these can be copolymerized with ionizable monomers, or with less hydrophilic species such as methylmethacrylate or other more hydrophobic monomers or macromonomers. Crosslinked linear polymer chains (i.e., macromolecules) based on these monomers may also be used in the second network, as well as biomacromolecules such as proteins and polypeptides (e.g., collagen, hyaluronic acid, or chitosan).

Other aspects of this invention are methods for bonding polyurethane to bone. In one embodiment, a telechelic polyurethane with photoreactive endgroups in an organic solvent with photoinitiator and crosslinker is coated onto a polyurethane. The solvent is removed under heat (e.g., 35 degrees Celsius) and convection for about 24-72 hours to yield a putty-like layer of end-linkable polyurethane layered on top of a preexisting polyurethane. Coating an existing polyurethane layer in this fashion effectively bonds the two materials together through packing of the hard segments of the two polyurethanes, effectively creating a single body. The putty is then pressed into a prepared surface of bone and the polyurethane exposed to a stimulus, such as UV light, to induce polymerization and crosslinking. This leads to mechanical interlocking of the polyurethane within the pores of the bone.

In some embodiments, the polyurethane is polycarbonate urethane or polyether urethane.

In some embodiments, the photoreactive endgroups on the polyurethane may be acrylamide, acrylate, allyl ether, methacrylate, or vinyl.

In some embodiments, the organic solvent may be dimethylacetamide, dimethyl sulfoxide, or tetrahydrofuran or combinations of these.

In some embodiments, the polyurethane may comprise a copolymer comprising linking monomers. The linking monomers may include acrylamide, dimethyl acrylamide, HEMA, triethylene glycol dimethacrylate, methyl methacrylate, and hydroxy ethyl acrylate (HEA). The linking monomers may improve the strength of the putty.

In another embodiment, salts are incorporated into the bone contacting layer. Any type of salt may be used. After incorporation of the putty into the bone and over time, the salts may be dissolved (e.g., NaCl) by body fluids or resorbed (e.g., tricalcium phosphate or carbonated apatite) by the body.

In some embodiments, the polyurethane may be attached to a hydrogel, such as described above.

In other embodiments, thermal, chemical-initiated or other methods of causing polymerization are used may be used to polymerize and crosslink the putty that has been pressed into a prepared surface of bone.

FIGS. 5A-C show how a telechelic adhesive polyurethane is deposited onto a first polyurethane. The adhesive polyurethane can be osteoconductive and/or porous.

FIG. 5A shows an adhesive telechelic polyurethane precursor 38 having hard segments 40, a soft segment 42, and functional endgroups 44 and 46. The endgroups 44 and 46 of the telechelic polyurethane can be the same or different structures. The telechelic polyurethane precursor can be a macromonomer with functional endgroups having any number of repeats "n" of the hard and soft segments as shown. For the purpose of illustration, the drawings in FIG. 5B and C show the simplest case in which the polyurethane precursor 38 is a single monomer with no repeats (n=1), but in practice the polyurethane precursor may have any number of repeating units (n>1). FIG. 5A also shows a material 50 with a polyurethane backing layer 52, and optionally a hydrogel layer 54 bonded to the polyurethane backing layer. The material 50 can be in the shape of a device such as for orthopedic use. In the presence of solvent 66, the polyurethane precursors 38 can be coated onto the surface of the material 50 to form an unreacted putty layer 70 on the polyurethane 52 with the putty layer and the backing layer held together by crystallization of the hard segments to create a single body 68, as shown in FIG. 5B. The putty layer is cured by treatment with UV light 74 and removal of solvent 76, to form a reacted adhesive 80 as shown in FIG. 5C. Optionally, salt 78 can be included in the reacted adhesive. The salt causes the material to be osteoconductive, or, after its removal, to form pores which allows for ingrowth of new bone.

In other embodiments, a foaming agent may be added to the polyurethane precursor solution or the second polyurethane to create open cell porosity. The porosity may vary in size, e.g., from about 10 μm to about 1000 μm.

In other embodiments, the solvent is removed prior to the UV curing step. In another embodiment, the solvent is removed after the UV curing step.

In other embodiments, thermal, chemical-initiated or other methods of effecting polymerization are used to coat the second polyurethane onto the first polyurethane-backed hydrogel following the process above.

In some embodiments, the reactive group of the second, telechelic polyurethane can be an acrylamide, acrylate, allyl ether, methacrylate, or vinyl group.

Figures 6A, 6B:
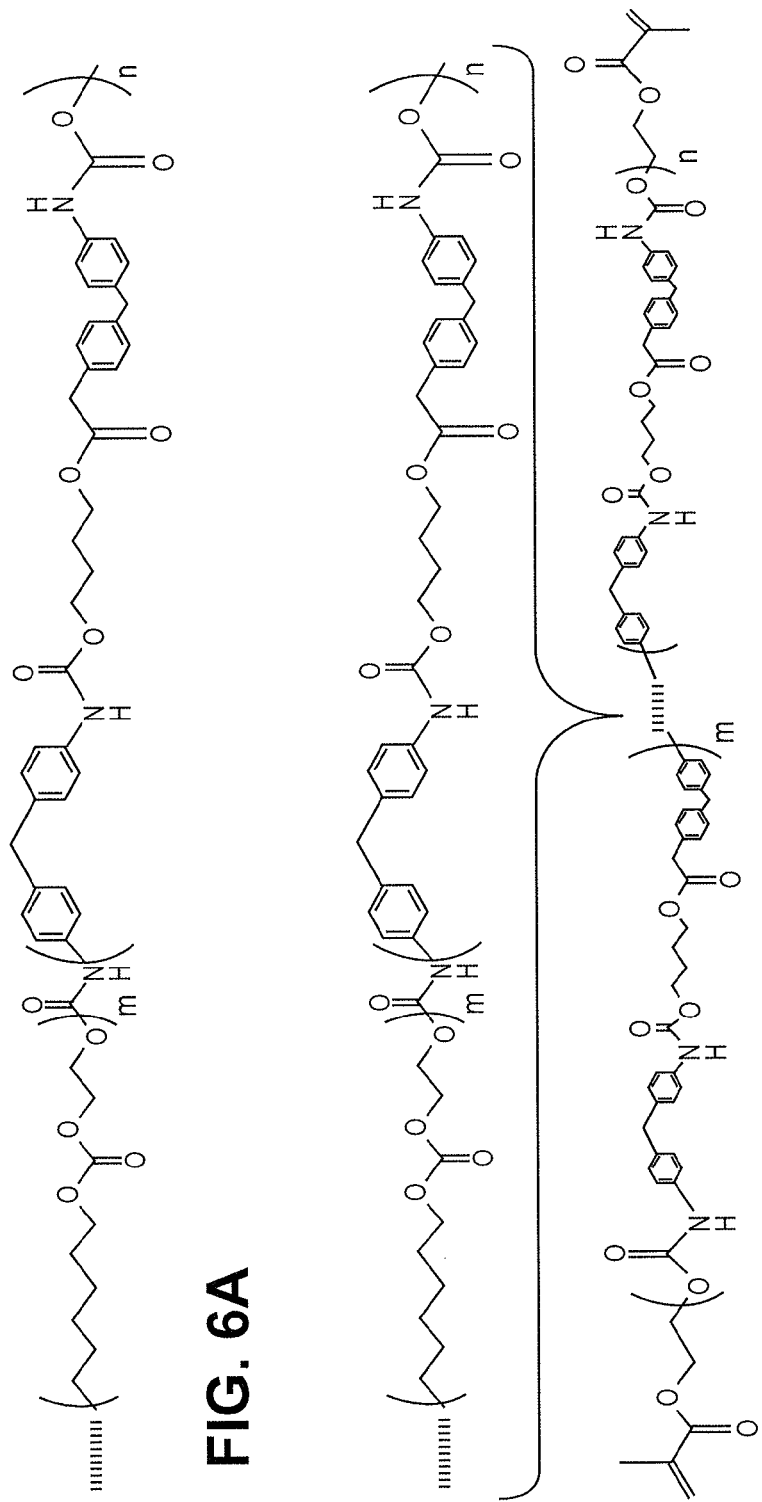
FIGS. 6A-B shows examples of the polyurethane backing material and polyurethane adhesive.

FIG. 6A-B show examples of materials that can be used in the present invention. FIG. 6A shows the structure of Bionate® polycarbonate-urethane that can be used in a polyurethane grafted hydrogel such as those as described in FIGS. 1 and 3, and as the backing material in FIG. 5. FIG. 6B shows Bionate® polycarbonate-urethane with acrylate functionalized end-groups that can be used as the adhesive layer such as described in FIGS. 5A-C. The lowercase "m" and "n" indicate that the polyurethane can have any number of soft and hard segments.

Figure 7A:
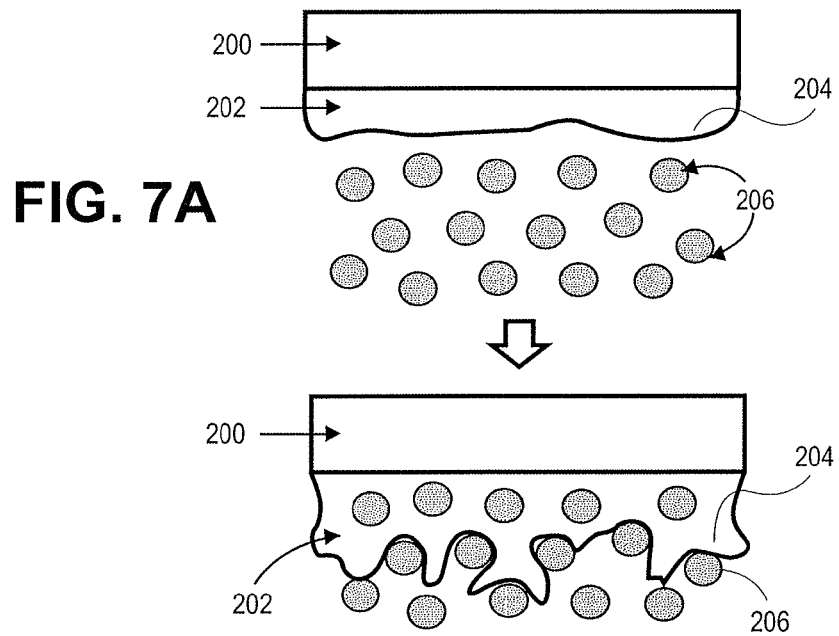
FIGS. 7A-D illustrate how the adhesive polyurethane attaches a material to bone according to one aspect of this invention
Figure 7B:
Figure 7C:
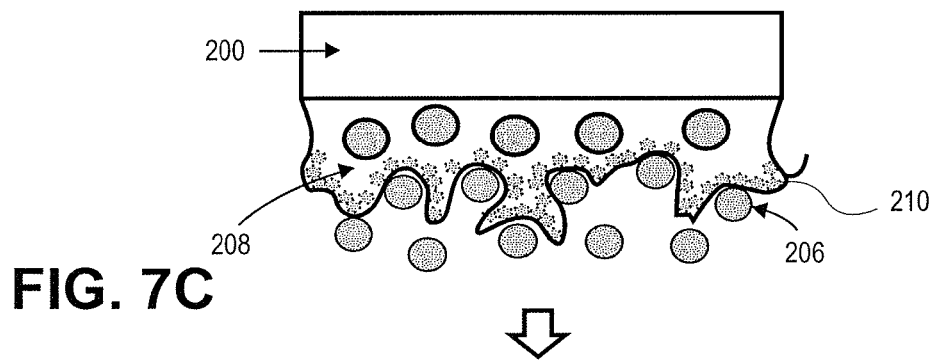
Figure 7D:
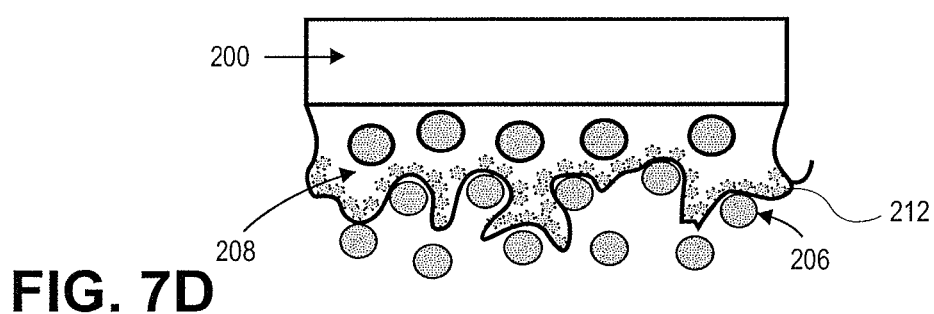

FIGS. 7A-C show a schematic of how a device can be attached to a bone using the polyurethane of the present invention. FIG. 7A shows a device, 200, such as an orthopedic device, with a layer of polyurethane adhesive or putty 202 which contains salt 204. The putty attached to the device is apposed to a prepared surface of bone 206, and the putty 202 is made to interdigitate around the bone 206, as shown in FIG. 7B. As shown in FIG. 7C, with the application of UV light 214 or other stimulus, the putty cures around the bone 208. With washing, or over time, the salt is removed, and pores 210 are left behind it its place. The pores provide a space for new bone growth 212 into the cured putty 208 as shown in FIG. 7D, thereby anchoring the device in place.

In addition, other therapeutic agents may also be incorporated into the putty, including but not limited to antibiotics and antimicrobials.

In another embodiment, a porous polyurethane is incorporated into the polyurethane backing layer of the present invention. This porous polyurethane can be incorporated by casting a salt-saturated (about 25%-90% by weight) solution of polyurethane in an organic solvent (about 10%-75% by weight) such as dimethylacetamide or dimethyl sulfoxide, evaporating the solvent under heat (e.g. 80° Celsius) and convection, and then washing the salt away in water. The salt can be any type of salt, including but not limited to sodium chloride or calcium phosphate or derivatives and/or combinations of these. The resulting porous backing layer can serve as a surface for attachment to bone using commercially available adhesives or cements (e.g., bone cements or dental cements) while also serving as a porous scaffold for bone ingrowth.

In some embodiments, biomolecules (e.g., collagen, growth factors (such as Bone Morphogenetic Proteins (BMPs)), Fibroblast Growth Factors (FGFs), Transforming Growth Factors (e.g., TGFβ), Osteogenic Proteins (e.g., OP-1 or osteopontin), steroids (e.g., dexamethasone), and bisphosphonates) may be incorporated into the device either as an additive or by covalent linkages, combinations, and/or derivatives thereof. Bone components may also be incorporated into the device, such as hydroxyapatite, carbonated apatite, alpha tricalcium phosphate, beta tricalcium phosphate, combinations, and/or derivatives thereof. The pore size useful for this application ranges between about 10 micrometers to 1000 micrometers.

In some embodiments, the porous polyurethane/polyurethane may be attached to other tissues (e.g., soft tissue, muscle, skin, dentin).

Figure 8A:
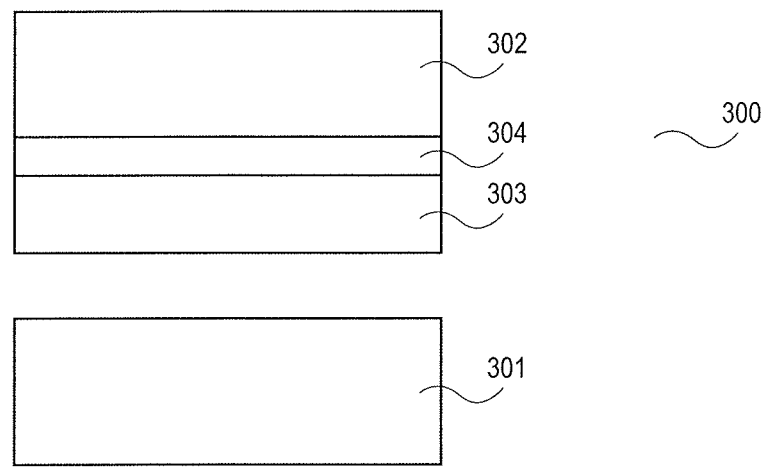
FIGS. 8A-B illustrate how the graft copolymer attaches to bone.
Figure 8B:
Figure 8B:
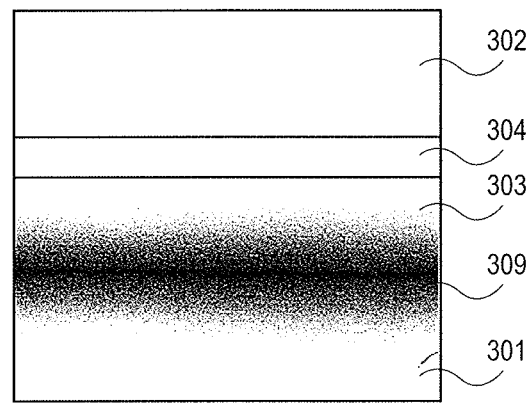

FIGS. 8A-B illustrate the integration of osteochondral grafts and other implants of this invention over time. In FIG. 8A, an osteochondral graft implant 300 formed as described above has a lubricious single network hydrogel polymer or IPN hydrogel surface 302 that transitions via a graft copolymer region 304 into the polyurethane polymer 303. The polyurethane polymer is the bone implant surface. The polyurethane, which may be porous and/or may contain salt is placed next to a bone 301. After implantation and over time, bone tissue will grow from bone 301 into and through the bone contacting surface 303, creating an overlap zone, 309, as illustrated in FIG. 8B.

Figure 9A:
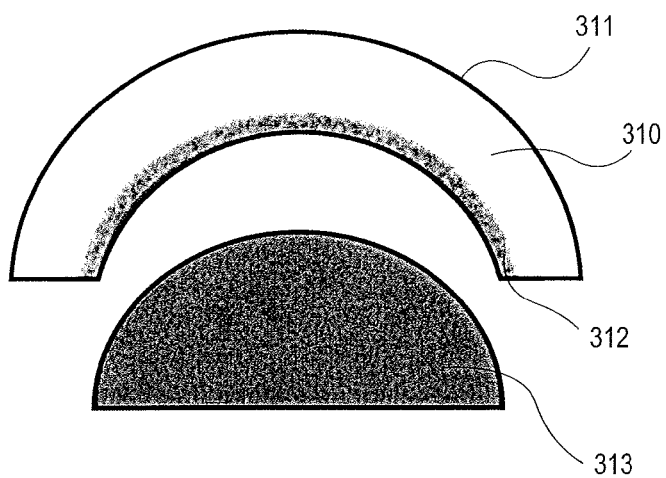
FIGS. 9A-C illustrate how an osteochondral graft implant formed from a polymer graft of this invention can be used to replace or augment cartilage within a joint.
Figure 9B:
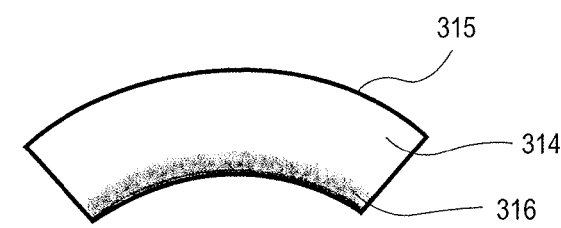
Figure 9B:
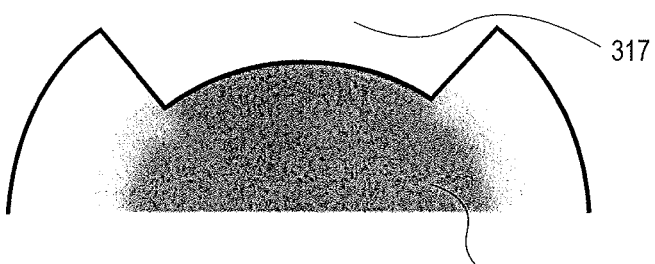
Figure 9C:
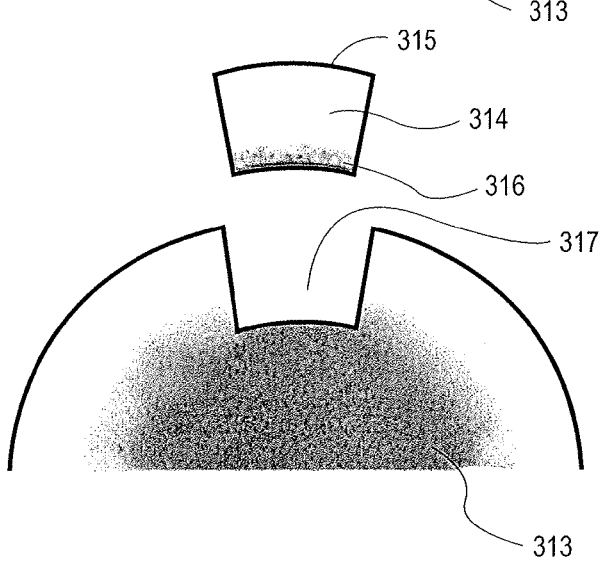

FIGS. 9A-C illustrate three possible configurations of osteochondral implants to repair cartilaginous join surface according to this invention. In FIG. 9A, implant 310 is formed as a cap having a lubricious network hydrogel or IPN hydrogel surface 311 transitioning via a graft copolymer region to a bone-contacting surface 312 formed from a polyurethane, as described above. When implanted, implant 310 covers the outer surface of bone 313.

FIGS. 9B and 9C show configurations in which implant 314 is formed as a patch or plug (respectively) having a lubricious network hydrogel polymer or IPN surface 315 transitioning via a graft copolymer region to a bone-contacting surface 316 formed from a polyurethane, as described above. When implanted, implant 314 fits within a prepared opening 317 of bone 313.

In another variation, a preexisting polymeric article (polyurethane or otherwise) can be dip casted in a solution of polyurethane with reactive end groups (monofunctional or telechelic). The dipcasted article can then be frozen as described above, and then dipped again in a solution of hydrogel monomers along with appropriate initiator and crosslinker. This can then be frozen a second time. The material would then be exposed to UV or other suitable stimulus to initiate polymerization and grafting of the hydrogel and the underlying derivatized PU layer. After drying and washing, the end result is a hydrogel grafted to the surface of the article through an intervening layer of polyurethane.

EXAMPLES

Example 1

Figure 10:
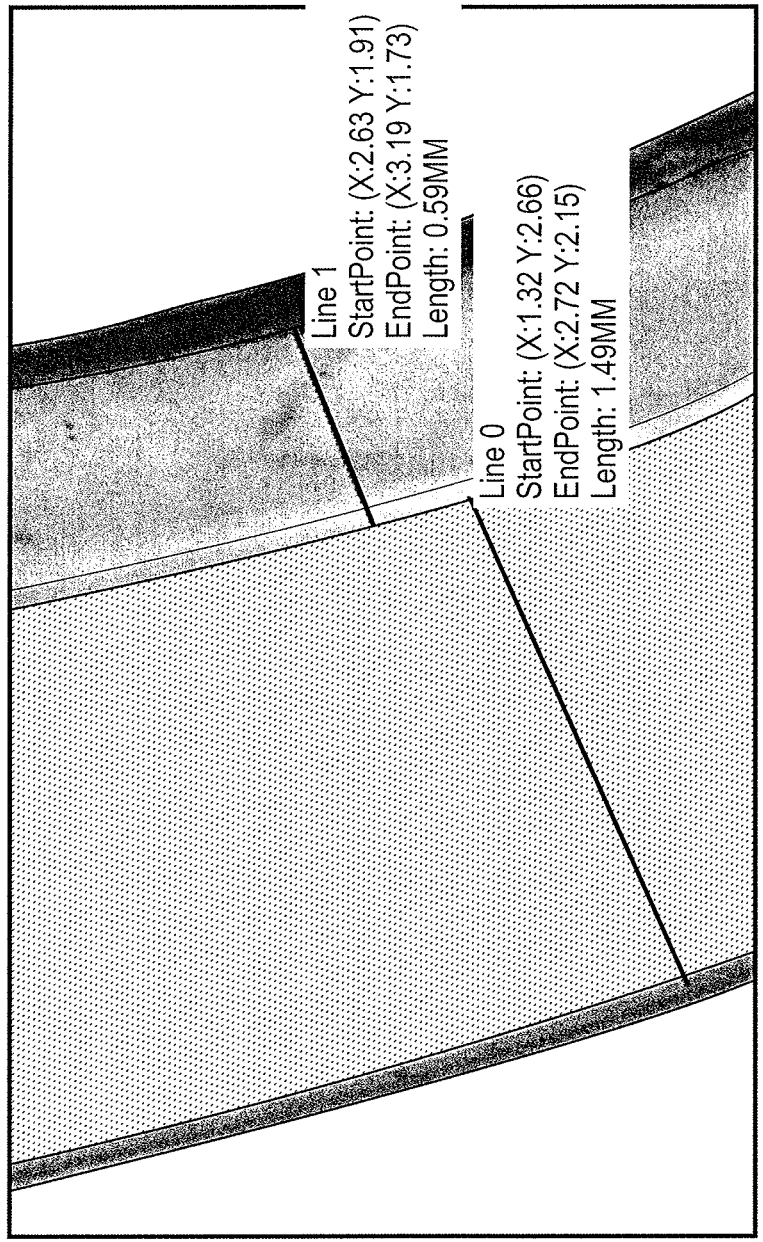
FIG. 10 is a shows a photomicrograph of a cross-section of the polyurethane-grafted hydrogel of a material made according to one aspect of this invention.

In one example, two polycarbonate-urethane grafted IPN hydrogels attached to polyurethane were made. The methods used were similar, and both are described here. Two specimens were separately synthesized by a two-step photopolymerization process using custom-made molds. The interpenetrating polymer network hydrogel components were synthesized by a two-step sequential network formation technique based on UV initiated free radical polymerization. The precursor solutions for the first hydrogel network were made of purified PEG-dimethacrylate (MW 3400) (43% by weight) dissolved in dimethylacetamide with 2-hydroxy-2-methyl propiophenone as the UV sensitive free radical initiator. The solutions were cast (separately) into custom-designed Pyrex glass molds, and then the solutions within the molds were flash-frozen in liquid nitrogen baths. 25% solutions of polycarbonate-urethane monomethacrylate (dissolved in dimethylacetamide) were spread over the frozen surfaces of the hydrogel solutions, each was covered with a glass plate, and they were reacted under a UV light source at room temperature. Upon exposure to UV (2 mW/cm2, 350 nm, 10 minutes), the hydrogel and polyurethane precursor solutions in each case underwent free-radical induced gelation while also grafting to each other due to endgroup compatibility. To incorporate the second hydrogel networks into the first, the polyurethane-grafted hydrogels were removed from the molds and immersed in 70% v/v acrylic acid solutions; in one case in organic solvent, and in the other case in water, along with 1% v/v 2-hydroxy-2-methyl propiophenone as the photoinitiator, and 1% v/v triethylene glycol dimethacrylate as the cross-linking agent for 24 h at room temperature. The swollen gels were exposed to a UV source and the second networks were polymerized inside the first networks to form an IPN structure in each polymer. Following synthesis, the polyurethane-grafted hydrogels were washed in dimethylacetamide, dried in a convection oven (80 degrees Celsius), and washed extensively in phosphate buffered saline with repeated solvent exchanges for 5 days to remove any unreacted components. One sample of one material was cut in cross section and analyzed by microscopy, as shown in FIG. 10. To add an additional layer of polyurethane to other samples, the surfaces of the polyurethane side of the hydrogels were air-dried, and then solutions of polycarbonate urethane (thermoplastic Bionate®; see FIG. 6) in dimethylacetamide were spread over the surface and the solvent evaporated by heat and convection. An analysis of the static mechanical properties of the cured and dried polyurethane containing precursors is shown in FIG. 11.

FIG. 10 shows a photomicrograph of a cross-section of the polyurethane-grafted hydrogel at 60× magnification. The hydrogel, on the left, is 1.5 mm thick, while the polyurethane on the right is 0.6 mm.

Figure 11:
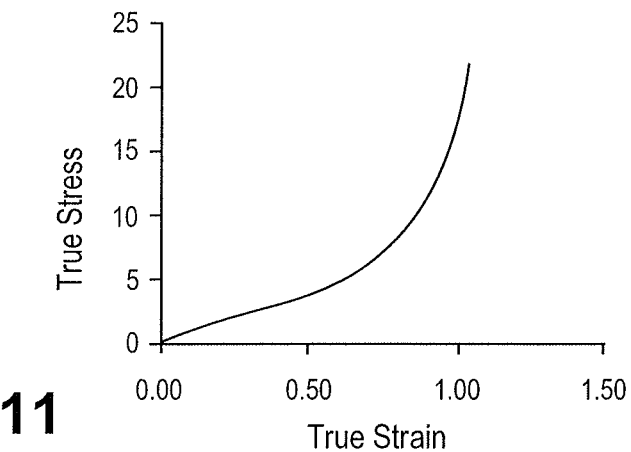
FIG. 11 shows the results of testing the static material properties of a material of the current invention.

FIG. 11 shows the results of testing of the static mechanical properties. Uniaxial tensile tests were conducted to determine the initial Young's modulus in tension, the strain-at-break, and stress-at-break of the materials. Dog bone specimens were tested following ASTM D638. The average true stress (in MPa)—true strain curve (in %) for the joint interface polyurethane material is presented in FIG. 11. The tensile strength is greater than 20 MPa.

Example 2

In another example, polyether urethane was used as the starting material. The material was made following the process described in Example 1.

Example 3

In another example, polyurethane layered onto another polyurethane was made and bonded to bone. Polycarbonate-urethane with methacrylate end groups was synthesized by reacting methylene diphenyl diisocyanate with polycarbonate diol (as the soft segment and 1,4 butanediol as the chain extender at a solid concentration of 30% in dimethylacetamide at 35 degrees Celsius. The monomer 2-hydroxyethyl methacrylate was added to the reaction mixture and the solution was reacted for an additional 24 hours). The resulting polycarbonate-urethane dimethacrylate was cast on the surface of a premade polycarbonate urethane (Bionate®) and the solvent removed at 35 degrees Celsius under convection.

After the solvent was removed, the unreacted polycarbonate-urethane dimethacrylate was pressed onto the surface of a previously prepared (cleaned and dried) bovine bone specimen, and exposed to UV light (2 mW/cm2, 350 nm, for 10 minutes). The result was polycarbonate urethane bonded to bone.

Figure 12:
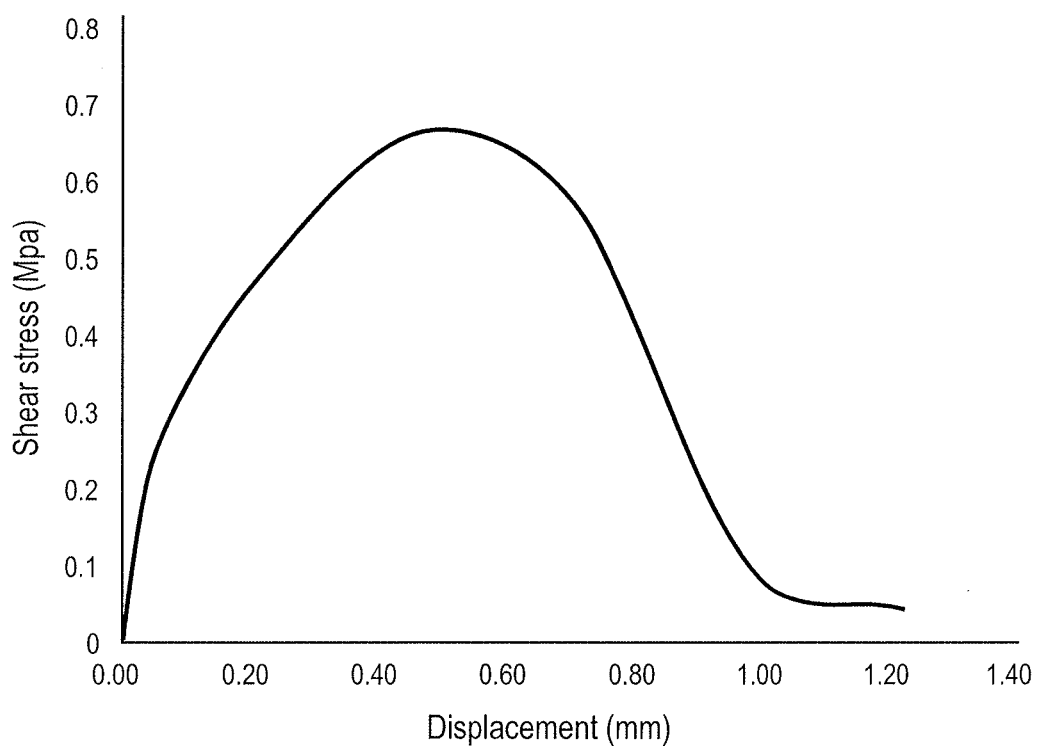
FIG. 12 shows the results of lap shear testing to determine the strength of material made according to the current invention.

The strength of the bonding was tested by performing a lap shear test, as described in ASTM D3163. Briefly, the lap shear test involved gripping the bone and the porous polyurethane graft and pulling them in opposite directions while collecting data. The shear stress (MPa) is plotted as a function of displacement (mm). As shown in FIG. 12, the shear stress necessary to remove the polyurethane from the bone was approximately 670 kPa. Testing of nine samples gave a mean (±S.D.) shear strength of 520±120 kPa.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of grafting a polyurethane layer to a hydrogel layer the method comprising the steps of:
   providing a first solution comprising either reactive hydrogel or end-functionalized polyurethane precursors;
   applying a second solution to the first solution wherein the second solution comprises end-functionalized polyurethane precursors if the first solution comprises hydrogel precursors and wherein the second solution comprises reactive hydrogel precursors if the first solution comprises polyurethane precursors; and
   polymerizing and crosslinking the solutions to form a laminated graft polymer comprising a polyurethane layer and a hydrogel layer.

2. The method of claim 1 further comprising freezing the first solution to form a solidified layer.

3. The method of claim 1 further comprising drying the first solution to form a solidified layer.

4. The method of claim 1 wherein the polymerizing step comprises exposing the first and second solutions to UV light or heat.

5. The method of claim 1 further comprising:
   swelling the hydrogel layer with a third solution comprising hydrogel precursors different from the precursors in the first or second solutions; and
   polymerizing the third solution to create a graft polymer comprising an IPN layer Comprising a second hydrogel network intertwined with a first hydrogel network and a polyurethane layer.

6. The method of claim 5 wherein the third solution comprises a partial solvent for the first hydrogel and is able to swell the first hydrogel network.

7. The method of claim 1 wherein the hydrogel solution comprises telechelic molecules.

8. The method of claim 7 wherein the telechelic molecules are poly(ethylene glycol) with one or more endgroups selected from the group consisting of acrylate, methacrylate, acrylamide, vinyl, and allyl ether.

9. The method of claim 1 wherein the polyurethane solution comprises one or more of vinyl terminated polyurethane, polycarbonate urethane, polyether urethane, polycarbonate urethane urea, polyester urethane, polyurethane urea and silicon derivatives of these.

10. The method of claim 1, further comprising covalently linking the hydrogel layer to the polyurethane layer at an interface between the two layers.

11. The method of claim 5, further comprising covalently linking the IPN layer to the polyurethane layer at an interface between the two layers.

12. A method of forming a laminated graft polymer having an end-fonetionalized polyurethane layer and a hydrogel layer comprising:
　　contacting a polyurethane precursor solution with a hydrogel precursor solution;
　　graft polymerizing the polyurethane precursor solution and the hydrogel precursor to form a laminated graft polymer having the end,funetionalized polyurethane layer covalently linked to the hydrogel layer at an interface between the two layers.

13. The method of claim 12, further comprising solidifying the polyurethane precursor solution.

14. The method of claim 13, wherein the polymerizing step generates heat to melt a portion of the solidified precursor solution.

15. The method of claim 12, further comprising solidifying the hydrogel precursor solution.

16. The method of claim 15, wherein the contacting step comprises casting the polyurethane precursor solution over a surface of the solidified hydrogel precursor solution.

17. The method of claim 15, wherein solidifying comprises flash freezing the hydrogel precursor solution.

18. The method of claim 12, further comprising crosslinking at least one of the hydrogel or polyurethane layers.

19. The method of claim 12, further comprising:
　　swelling the hydrogel layer with another hydrogel precursor solution; and
　　polymerizing the another hydrogel precursor solution inside the hydrogel layer to form a hydrogel IPN inside the hydrogel layer.

20. The method of claim 12, wherein the polyurethane precursor solution comprises one or more of vinyl terminated polyurethane, polycarbonate urethane, polyether urethane, polycarbonate urethane urea, polyester urethane, polyurethane urea and silicon derivatives of these.

* * * * *